(12) United States Patent
Hosoya et al.

(10) Patent No.: US 8,932,853 B2
(45) Date of Patent: Jan. 13, 2015

(54) METHOD FOR MANUFACTURING PANCREATIC-HORMONE-PRODUCING CELLS

(75) Inventors: Masaki Hosoya, Kanagawa (JP); Yuya Kunisada, Kanagawa (JP); Masanobu Shoji, Kanagawa (JP); Noriko Yamazoe, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 40 days.

(21) Appl. No.: 13/520,090

(22) PCT Filed: Dec. 28, 2010

(86) PCT No.: PCT/JP2010/073906
§ 371 (c)(1),
(2), (4) Date: Sep. 28, 2012

(87) PCT Pub. No.: WO2011/081222
PCT Pub. Date: Jul. 7, 2011

(65) Prior Publication Data
US 2013/0022986 A1 Jan. 24, 2013

(30) Foreign Application Priority Data

Dec. 29, 2009 (JP) .................................. 2009-299276
Jun. 24, 2010 (JP) .................................. 2010-144283

(51) Int. Cl.
C12N 5/00 (2006.01)
C12N 5/071 (2010.01)
C12N 5/02 (2006.01)
G01N 33/50 (2006.01)
A61K 35/39 (2006.01)

(52) U.S. Cl.
CPC ............ *C12N 5/0676* (2013.01); *G01N 33/507* (2013.01); *A61K 35/39* (2013.01); *C12N 2501/155* (2013.01); *C12N 2501/16* (2013.01); *C12N 2501/385* (2013.01); *C12N 2501/727* (2013.01)
USPC ............................ 435/325; 435/366; 435/377

(58) Field of Classification Search
CPC ..... A61K 38/00; A61K 35/12; C12N 2506/12
USPC .......................................... 435/325, 366, 377
See application file for complete search history.

(56) References Cited

U.S. PATENT DOCUMENTS

| | | | |
|---|---|---|---|
| 5,942,435 A * | 8/1999 | Wheeler | 435/325 |
| 6,326,201 B1 | 12/2001 | Fung et al. | |
| 7,033,831 B2 | 4/2006 | Fisk et al. | |
| 7,326,572 B2 | 2/2008 | Fisk et al. | |
| 7,534,608 B2 * | 5/2009 | Martinson et al. | 435/377 |
| 2003/0138948 A1 | 7/2003 | Fisk et al. | |
| 2003/0138949 A1 | 7/2003 | Bhushan et al. | |
| 2005/0266555 A1 | 12/2005 | Lu et al. | |
| 2006/0040387 A1 | 2/2006 | Fisk et al. | |
| 2008/0145889 A1 | 6/2008 | Fisk et al. | |
| 2008/0207594 A1 * | 8/2008 | Mussmann et al. | 514/215 |
| 2009/0093055 A1 | 4/2009 | Fisk et al. | |
| 2009/0325180 A1 | 12/2009 | Fisk et al. | |

FOREIGN PATENT DOCUMENTS

| | | |
|---|---|---|
| JP | 2002-538779 A | 11/2002 |
| JP | 2006-500003 A | 1/2006 |
| JP | 2006-506047 A | 2/2006 |
| JP | 2006-075022 A | 3/2006 |
| JP | 2009-225661 A | 10/2009 |
| WO | WO-00/47720 A2 | 8/2000 |
| WO | WO-03/050249 B1 | 6/2003 |
| WO | WO-03/100026 A2 | 12/2003 |
| WO | WO-2007/113505 A2 | 10/2007 |
| WO | WO-2008/015418 A2 | 2/2008 |

(Continued)

OTHER PUBLICATIONS

Xu et al., cited on IDS Jun. 29, 2012, reference BA.*

(Continued)

*Primary Examiner* — Anoop Singh
*Assistant Examiner* — David A Montanari
(74) *Attorney, Agent, or Firm* — Edwards Wildman Palmer LLP; George W. Neuner

(57) ABSTRACT

The present invention provides a method of more efficiently producing pancreas cells, particularly pancreatic hormone-producing cells, a method of stably producing pancreas cells in a large amount by more efficiently inducing differentiation of stem cells into pancreas cells, a medicament containing a pancreas cells and a screening method using the cells.

A method of producing pancreatic hormone-producing cells, including subjecting stem cells to the following steps (1)-(4):

(1) a step of cultivating stem cells in a medium containing an activator of activin receptor-like kinase-4,7 and a GSK3 inhibitor (2) a step of cultivating the cells obtained in the aforementioned step (1) in a medium containing an activator of activin receptor-like kinase-4,7

(3) a step of cultivating the cells obtained in the aforementioned step (2) in a medium containing any one or more kinds selected from the group consisting of (a) retinoic acid receptor agonists, (b) at least one kind selected from the group consisting of inhibitors of AMP-activated protein kinase and/or activin receptor-like kinase-2,3,6, and BMP antagonists, and (c) inhibitors of activin receptor-like kinase-4,5,7

(4) a step of cultivating the cells obtained in the aforementioned step (3).

10 Claims, 21 Drawing Sheets

(56) References Cited

FOREIGN PATENT DOCUMENTS

| WO | WO-2008/033408 A2 | 3/2008 | |
|---|---|---|---|
| WO | WO-2008/066199 A1 | 6/2008 | |
| WO | WO-2009/012428 A2 | 1/2009 | |
| WO | WO 2009/018453 * | 2/2009 | ............... C12N 5/06 |
| WO | WO-2009/018453 A1 | 2/2009 | |
| WO | WO-2009/070592 A2 | 6/2009 | |

OTHER PUBLICATIONS

NIH Adult Stem Cell Guidelines.*
NIH Embryonc Stem Cell Guidelines.*
Brevini et al., 2010, Theriogenology, vol. 74, pp. 544-550.*
Paris et al., 2010, Theriogenology, vol. 74, pp. 516-524.*
Munoz et al., 2008, Theriogenology, vol. 69, pp. 1159-1164.*
Hao et al. (2008, PLoS One, vol. 3(8), pp. 1-8).*
Rafacho et al. (2009, Am. J. Physiol. Endocrinol. Metab., vol. 296, pp. E681-E689).*
D'Amour et al. (2006, Nature Biotechnology, vol. 24(11), pp. 1392-1401).*
Wrighton, K.H. et al., Transforming Growth Factor β Can Stimulate SMADL Phosphorylation Independently of Bone Morphogenic Protein Receptors, J. Biol. Chem., 2009, vol. 284, No. 15, p. 9755-9763.
Yu, P.B. et al. Dorsomorphin Inhibits BMP Signals Required for Embryogenesis and Iron Metabolism, Nat. Chem. Biol., 2008, vol. 4, No. 1, p. 33-41.
Kroon, E. et al., Pancreatic Endoderm Derived From Himan Embryonic Stem Cells Generates Glucose-Responsive Insulin-Secreting Cells in Vivo, Nature Biotech. 26, 2008, p. 443-452.
D'Amour, K. et al., Production of Pancreatic Hormone-Expressing Endocrine Cells From Human Embryonic Stem Cells, Nature Biotech. 24, 2006, p. 1392-1401.
Jiang, W., et al., In Vitro Derivation of Functional Insulin-Producing Cells From Human Embryonic Stem Cells, Cell Research 17, 2007, p. 333-344.
Maehr, R. et al., Generation of Pluripotent Stem Cells From Patients With Type 1 Diabetes, PNAS 106, 2009, p. 15768-15773.
Shim, J.H. et al., Directed Differentiation of Human Embryonic Stem Cells Towards a Pancreatic Cell Fate, Diabetologia 50, 2007, p. 1228-1238.
Rezania, A., et al., Production of Functional Glucagon-Secreting α-Cells From Human Embryonic Stem Cells, Diabetes 60, 2011, p. 239-247.
Kume et al, BMB2010 Biochemistry and Molecular Biology (3P-0861; Abstract).
International Search Report from PCT/JP2010/073906.

\* cited by examiner

Ctrl : Control
Act : Comparative Example 1
Act+Wnt : Comparative Example 2
Act+CHIR : Example 1

Ctrl : Control
RA : Example 39
Nog : Example 40
DM : Example 41
Nog+RA: Example 42
DM+RA  Example 43

Ctrl : Control
SB431542:Example 44
Alk5 inhibitor II:Example 45
A-83-01: Example 46
TGFβRI kinase inhibitor VIII:Example 47

METHOD FOR MANUFACTURING PANCREATIC-HORMONE-PRODUCING CELLS

CROSS-REFERENCE TO RELATED APPLICATIONS

This application is a §371 U.S. National Stage Application of copending International Patent Application PCT/JP2010/073906 which was filed on Dec. 28, 2010, and which in turn claims priority to Japanese Patent Application No. 299276/2009 which was filed on Dec. 29, 2009 and Japanese Patent Application No. 144283/2010 which was filed on Jun. 24, 2010, each of which is incorporated herein by reference in its entirety.

TECHNICAL FIELD

The present invention relates to a production method of pancreatic hormone-producing cells. The present invention further relates to pancreatic hormone-producing cells obtained by the method, a screening method of a medicament using the cells, a medicament using the cells and the like.

BACKGROUND OF THE INVENTION

Pancreas has endocrine glands (endocrine cells) and exocrine glands (exocrine cells), and is an organ playing an important role in the both secretory cells. Exocrine cells mainly play a role of secreting digestive enzymes such as pancreatic lipase, trypsin, elastase, pancreatic amylase and the like.

Endocrine cells play a role of secreting pancreatic hormone, and it is known that glucagon is secreted from pancreatic α cells, insulin is secreted from pancreatic β cells, somatostatin is secreted from pancreatic δ cells, and pancreatic polypeptide (PP) is secreted from PP cells. In recent years, it has been reported that ghrelin, which is a stomach-secreted hormone is also secreted from endocrine cells of the pancreas.

Insulin plays an important role of promoting utilization of glucose, protein synthesis, and formation and storage of neutral fats, lowering blood glucose level, and maintaining blood glucose at a correct concentration. Glucagon plays an important role, along with insulin, in a sugar metabolism regulatory mechanism, as a hyperglycemic hormone via hepatic glycogenolysis, gluconeogenesis action and the like. Somatostatin expresses an action by binding to a somatostatin receptor, and suppresses secretion of various hormones such as glucagon, insulin and the like in the pancreas. PP is a hormone secreted from the cells of Langerhans' islets in response to diet, known as a satiety factor, and reduces food ingestion and body weight gain. Ghrelin is known to stimulate food ingestion, and increase body weight gain by reducing fat oxidation.

Diabetes is a disease developed by insufficient insulin and loss of the function thereof, and difficult to cure once it is developed. Diabetes can be largely classified into two types of type I diabetes mellitus (insulin dependent diabetes) and type II diabetes mellitus (non-insulin dependent diabetes).

Type II diabetes mellitus is a chronic disease developed by resistance to insulin, which becomes problems in relation to lifestyle habits such as obesity due to overeating and inactivity, stress etc. Type II diabetes mellitus is often developed in middle-aged adults, and many of the diabetes patients are affected with type II diabetes.

Type I diabetes mellitus is a chronic disease caused by destruction of pancreatic β cells (sometimes referred to as insulin-producing cells in the present specification) by autoimmune diseases, virus infection and the like to terminate secretion of insulin in the body. As a treatment method that can automatically control blood glucose level that continuously changes in the body and reduce burden on patients, pancreas transplantation or pancreatic islet transplantation is performed on patients with type I diabetes mellitus. While it is possible to achieve a normal blood glucose level by these treatment methods, the transplantation technique has not been sufficiently established, and the pancreas and pancreatic islet that can be transplanted are not sufficient. Moreover, to avoid immune rejection to a graft, the patients need to take an immunosuppressant for the entire life, and the problems of the risk of infection, side effects caused by immunosuppressant and the like still remain.

One of the treatment methods tried for type I diabetes mellitus is a method inducing insulin-producing cells itself in vitro from cells derived from a patient, and transplanting the induced insulin-producing cells into the body of the patient. According to this method, insulin can be produced in the body of the patient. When insulin-producing cells are induced from cells derived from a patient, it is advantageous from the aspect of safety. Since the cells are derived from the patient, the problem of immune rejection etc. can be resolved.

Known methods for obtaining insulin-producing cells include a method of differentiating embryonic stem cells (sometimes to be referred to ES cells in the present specification), a method of differentiating induced pluripotent stem cells (sometimes referred to iPS cells in the present specification), a method of differentiating tissue stem cells of the pancreas of a patient, a method of extracting cells derived from the pancreatic duct epithelium of a patient in vitro and differentiating the same and the like. Specifically, a method of inducing differentiation of pancreatic β cells from human ES cells by using activin and retinoic acid (RA) (patent document 1, non-patent documents 1-4), a method of inducing differentiation of pancreatic β cells from human iPS cells (non-patent document 5), a method of efficiently inducing differentiation of insulin-producing cells, including introducing PDX1, which is known to be an important transcription factor involved in the development of the pancreas and also responsible for the development and function maintenance of insulin-producing cells, into ES cells, and cultivating the cells (patent documents 2-3), and a method including dedifferentiating hormone non-producing pancreatic cells to give stem cells, and inducing differentiation of the stem cells by using activin and RA (patent document 4).

However, since the insulin-producing cells obtained by these methods show considerably low insulin production efficiency as compared to those of normal pancreatic β cells, the development of a method of efficiently obtaining functional insulin-producing cells is still demanded. In addition, to perform treatment of diabetes and the like, the development of a method of obtaining a sufficient number of pancreatic hormone-producing cells (including insulin-producing cells) is demanded.

DOCUMENT LIST

Patent Documents

[patent document 1] JP-A-2009-225661
[patent document 2] U.S. Pat. No. 7,534,608
[patent document 3] JP-A-2006-075022
[patent document 4] WO03/100026

Non-Patent Documents

[non-patent document 1] E. Kroon et al., "Pancreatic endoderm derived from human embryonic stem cells generates glucose-responsive insulin-secreting cells in vivo", Nature Biotechnology (2008) Vol. 26, No. 4: 443-452

[non-patent document 2] K. A. D'Amour et al., "Production of pancreatic hormone-expressing endocrine cells from human embryonic stem cells", Nature Biotechnology (2006) Vol. 24, No. 11: 1392-1401

[non-patent document 3] W. Jiang, "In vitro derivation of functional insulin-producing cells from human embryonic stem cells", Cell Research (2007) 17: 333-344

[non-patent document 4] J. H. Shim et al., "Directed differentiation of human embryonic stem cells towards a pancreatic cell fate", Diabetologia (2007) 50:1228-1238

[non-patent document 5] R. Maehra et al., "Generation of pluripotent stem cells from patients with type 1 diabetes", PNAS (2009), vol. 106, No. 37: 15768-15773

SUMMARY OF THE INVENTION

Problems to be Solved by the Invention

An object of the present invention is to provide a method of more efficiently producing pancreatic hormone-producing cells, more preferably, to stably produce pancreatic hormone-producing cells in a large amount by more efficiently inducing differentiation of stem cells into pancreatic hormone-producing cells. Furthermore, the present invention aims to provide a screening method of a medicament, which uses pancreatic hormone-producing cells obtained by the method of the present invention, and a medicament using the same.

Means of Solving the Problems

In view of the above-mentioned problem, the present inventors have conducted intensive studies and found that differentiation of stem cells to pancreatic hormone-producing cells can be induced more efficiently by stepwisely changing the kind and combination of differentiation-inducing factors, and confirmed the function of the obtained pancreatic hormone-producing cells, which resulted in the completion of the present invention.

Accordingly, the present invention provides the following.

[1] A method of producing a pancreatic hormone-producing cell(s), comprising subjecting a stem cell(s) to the following steps (1)-(4):
(1) a step of cultivating a stem cell(s) in a medium containing an activator of activin receptor-like kinase-4,7 and a GSK3 inhibitor
(2) a step of cultivating the cell(s) obtained in the aforementioned step (1) in a medium containing an activator of activin receptor-like kinase-4,7
(3) a step of cultivating the cell(s) obtained in the aforementioned step (2) in a medium containing any one or more kinds selected from the group consisting of (a) retinoic acid receptor agonists, (b) at least one kind selected from the group consisting of inhibitors of AMP-activated protein kinase and/or activin receptor-like kinase-2,3,6, and BMP antagonists, and (c) inhibitors of activin receptor-like kinase-4,5,7
(4) a step of cultivating the cell(s) obtained in the aforementioned step (3);
[2] the production method of the above-mentioned [1], wherein the activator of activin receptor-like kinase-4,7 in steps (1) and (2) is activin, and step (3) is a step of cultivating the cell(s) obtained in step (2) in a medium containing any one or more kinds selected from the group consisting of (a) retinoic acid receptor agonists, (b') inhibitors of AMP-activated protein kinase and/or activin receptor-like kinase-2,3,6 and (c) inhibitors of activin receptor-like kinase-4,5,7;
[3] the production method of the above-mentioned [1] or [2], wherein step (4) is performed in a medium containing any one or more kinds selected from the group consisting of (i) at least one kind selected from the group consisting of adenylate cyclase activators, cAMP phosphodiesterase inhibitors and cAMP analogs, (ii) steroids and (iii) inhibitors of activin receptor-like kinase-4,5,7;
[4] a method of producing an endodermal cell(s), comprising cultivating a stem cell(s) in a medium containing at least an activator of activin receptor-like kinase-4,7 and a GSK3 inhibitor;
[5] the production method of the above-mentioned [4], wherein the activator of activin receptor-like kinase-4,7 is activin;
[6] a method of producing a progenitor cell(s) of a pancreatic hormone-producing cell(s), comprising cultivating an endodermal cell(s) in a medium containing any one or more kinds selected from the group consisting of the following (a)-(c):
(a) retinoic acid receptor agonists
(b) at least one kind selected from the group consisting of inhibitors of AMP-activated protein kinase and/or activin receptor-like kinase-2,3,6, and BMP antagonists, and
(c) inhibitors of activin receptor-like kinase-4,5,7;
[7] a method of producing a progenitor cell(s) of a pancreatic hormone-producing cell(s), comprising cultivating an endodermal cell(s) in a medium containing the following (a)-(c):
(a) a retinoic acid receptor agonist
(b) at least one kind selected from the group consisting of inhibitors of AMP-activated protein kinase and/or activin receptor-like kinase-2,3,6, and BMP antagonists, and
(c) an inhibitor of activin receptor-like kinase-4,5,7;
[8] the production method of any of the above-mentioned [1] to [3], wherein the medium in step (3) contains the following (a)-(c):
(a) a retinoic acid receptor agonist
(b) at least one kind selected from the group consisting of inhibitors of AMP-activated protein kinase and/or activin receptor-like kinase-2,3,6, and BMP antagonists, and
(c) an inhibitor of activin receptor-like kinase-4,5,7;
[9] the production method of any of the above-mentioned [1] to [3] and [8], wherein the GSK3 inhibitor in step (1) is 6-[[2-[[4-(2,4-dichlorophenyl)-5-(4-methyl-1H-imidazol-2-yl)-2-pyrimidinyl]amino]ethyl]amino]nicotinonitrile;
[10] the production method of any of the above-mentioned [1] to [3], [8] and [9], wherein the inhibitor of activin receptor-like kinase-4,5,7 in step (3) is 4-[4-(1,3-benzodioxol-5-yl)-5-(2-pyridinyl)-1H-imidazol-2-yl]-benzamide or a hydrate thereof;
[11] the production method of any of the above-mentioned [1] to [3] and [8] to [10], wherein said at least one kind selected from the group consisting of inhibitors of AMP-activated protein kinase and/or activin receptor-like kinase-2,3,6, and BMP antagonists in step (3) is dorsomorphin or Noggin;
[12] the production method of any of the above-mentioned [1] to [3] and [8] to [11], wherein the medium in step (3) contains retinoic acid, 4-[4-(1,3-benzodioxol-5-yl)-5-(2-pyridinyl)-1H-imidazol-2-yl]-benzamide or a hydrate thereof, and dorsomorphin;

[13] the production method of any of the above-mentioned [3] and [8] to [12], wherein at least one kind selected from the group consisting of adenylate cyclase activators, cAMP phosphodiesterase inhibitors and cAMP analogs is forskolin, 3-isobutyl-1-methylxanthine or dibutyl cAMP;

[14] the production method of any of the above-mentioned [3] and [8] to [13], wherein the steroid is dexamethasone;

[15] the production method of any of the above-mentioned [3] and [8] to [14], wherein the inhibitor of activin receptor-like kinase-4,5,7 is 2-(3-(6-methylpyridin-2-yl)-1H-pyrazol-4-yl)-1,5-naphthyridine, or 4-[4-(1,3-benzodioxol-5-yl)-5-(2-pyridinyl)-1H-imidazol-2-yl]-benzamide or a hydrate thereof;

[16] the production method of any of the above-mentioned [3] and [8] to [15], wherein the medium contains nicotinamide;

[17] the production method of any of the above-mentioned [1] to [5] and [8] to [16], wherein the stem cell(s) is(are) an induced pluripotent stem cell(s) (iPS cell(s)), an embryonic stem cell(s) (ES cell(s)) or a human somatic stem cell(s);

[18] the production method of any of the above-mentioned [1] to [5] and [8] to [17], wherein the pancreatic hormone-producing cell(s) is(are) any selected from the group consisting of insulin-producing cells, glucagon-producing cells, somatostatin-producing cells, pancreatic polypeptide (PP)-producing cells and ghrelin-producing cells;

[19] a medicament comprising the pancreatic hormone-producing cell(s) obtained by the production method of any of the above-mentioned [1] to [5] and [8] to [18];

[20] a medicament comprising the progenitor cell(s) of the pancreatic hormone-producing cell(s) obtained by the production method of the above-mentioned [6] or [7];

[21] a method of screening for a therapeutic drug for diabetes, comprising using the cell(s) obtained by any one or more steps selected from the group consisting of the following steps (1)-(4):

(1) a step of cultivating a stem cell(s) in a medium containing an activator of activin receptor-like kinase-4,7 and a GSK3 inhibitor (2) a step of cultivating the cell(s) obtained in the aforementioned step (1) in a medium containing an activator of activin receptor-like kinase-4,7

(3) a step of cultivating the cell(s) obtained in the aforementioned step (2) in a medium containing any one or more kinds selected from the group consisting of (a) retinoic acid receptor agonists, (b) at least one kind selected from the group consisting of inhibitors of AMP-activated protein kinase and/or activin receptor-like kinase-2,3,6, and BMP antagonists, and (c) inhibitors of activin receptor-like kinase-4,5,7

(4) a step of cultivating the cell(s) obtained in the aforementioned step (3);

[22] the screening method of the above-mentioned [21], wherein the activator of activin receptor-like kinase-4,7 in steps (1) and (2) is activin, and step (3) is a step of cultivating the cell(s) obtained in step (2) in a medium containing any one or more kinds selected from the group consisting of (a) retinoic acid receptor agonists, (b') inhibitors of AMP-activated protein kinase and/or activin receptor-like kinase-2,3,6, and (c) inhibitors of activin receptor-like kinase-4,5,7; and

[23] the screening method of the above-mentioned [21] or [22], wherein step (4) is performed in a medium containing one or more kinds selected from the group consisting of (i) at least one kind selected from the group consisting of adenylate cyclase activators, cAMP phosphodiesterase inhibitors and cAMP analogs, (ii) steroids and (iii) inhibitors of activin receptor-like kinase-4,5,7.

Effect of the Invention

According to the present invention, pancreatic hormone-producing cells can be more efficiently produced from stem cells. Pancreatic hormone-producing cells produced by the present invention can be used for screening for a compound useful for the prophylaxis and/or treatment of a disease caused by abnormality of pancreatic hormone production and/or secretion, such as diabetes and the like. Moreover, pancreatic hormone-producing cells obtained by the production method of the present invention can be used for a cell therapy for treating such diseases.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
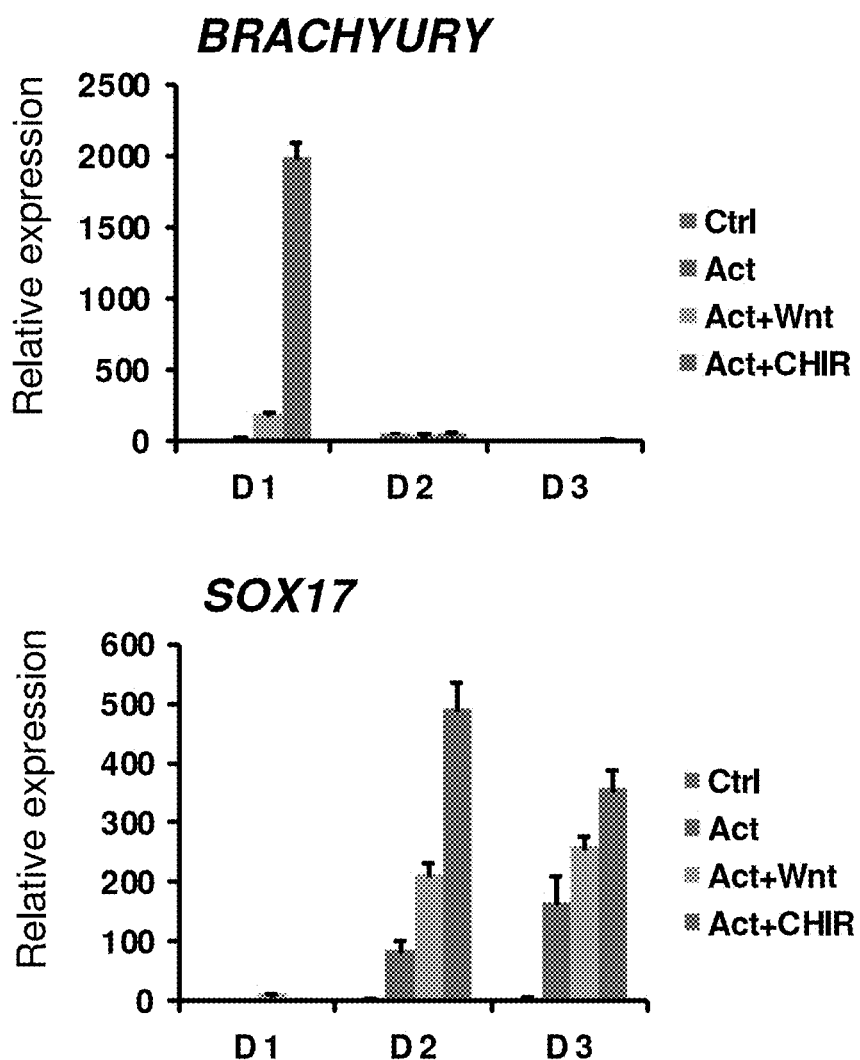
FIG. 1 shows the results obtained by initiating induction of differentiation from human iPS cells by using various factors, and measuring the expression of a primitive streak marker (Brachyury) and an endodermal marker (SOX17) every day for the first 3 days by quantitative RT-PCR. The expression levels of each gene when no differentiation-inducing factor was added (Ctrl), when activin A alone was added for 3 days (Act: Comparative Example 1), when activin A (3 days) and Wnt3a (only the first day) were added (Act Wnt: Comparative Example 2), and when activin A (3 days) and CHIR99021 (only the first day) were added (Act CHIR: Example 1) are shown as relative values to the expression level of a housekeeping gene GAPDH. The expression of Brachyury showed the highest value on day 1 of differentiation induction with the combination of activin A and CHIR99021, and SOX17 showed a high value on days 2-3 of differentiation induction with the combination of activin A and Wnt3a or CHIR99021.

The present invention is explained in the following. The terms used in the present specification mean those generally used in the field, unless particularly specified.

In the present specification, examples of the "pancreatic hormone" include insulin, glucagon, somatostatin, pancreatic polypeptide and ghrelin.

In the present specification, "pancreatic hormone-producing cells" means cells having an ability to produce a pancreatic hormone. The pancreatic hormone-producing cells do not need to constantly produce a pancreatic hormone, but only needs to have an ability to produce a pancreatic hormone. In addition, the amount of the pancreatic hormone to be produced is not particularly limited.

Examples of the "pancreatic hormone" of the "pancreatic hormone-producing cells" include those exemplified above as the "pancreatic hormone" in the present specification. Specific examples of the "pancreatic hormone-producing cells" include insulin-producing cells, glucagon-producing cells (sometimes to be referred to as pancreatic α cells in the present specification), somatostatin-producing cells (sometimes to be referred to as pancreatic δ cells in the present specification), PP-producing cells and ghrelin-producing cells.

In the present specification, the "stem cells" means cells that can be cultivated in vitro, and can be differentiated into plural cell lines constituting the body. Specifically, ES cells, pluripotent stem cells derived from primordial germ cells of embryo (EG cell: Proc Natl Acad Sci USA. 1998, 95:13726-31), testis-derived pluripotent stem cells (GS cells: Nature. 2008, 456: 344-9), somatic cell-derived induced pluripotent stem cells (induced pluripotent stem cells; iPS cells) and human somatic stem cells (tissue stem cells) can be mentioned. Preferred are iPS cells, ES cells and human somatic stem cells, and more preferred is iPS cells.

As the ES cells, ES cells derived from any warm-blooded animal, preferably mammal, can be used. Examples of the mammal include mouse, rat, guinea pig, hamster, rabbit, cat, dog, sheep, swine, bovine, horse, goat, monkey and human. Preferable examples of the ES cells include ES cells derived from human.

Specific examples of the ES cells include ES cells of a mammal and the like, which is established by cultivating an early embryo before implantation, ES cells established by cultivating an early embryo prepared by nuclear transplantation of the nuclei of somatic cells, and ES cells obtained by altering the gene on the chromosome of such ES cells by genetic engineering.

Each ES cell can be prepared by a method generally performed in the field or according to a known document.

ES cells of a mouse were established in 1981 by Evans et al. (Evans et al., 1981, Nature 292: 154-6) and Martin et al. (Martin G R. et al., 1981, Proc Natl Acad Sci 78: 7634-8) and can be purchased from, for example, Dainippon Sumitomo Pharma Co., Ltd. (Osaka, Japan) and the like.

ES cells of a human were established in 1998 by Thomson et al. (Thomson et al., Science, 1998, 282:1145-7), and can be obtained from WiCell Research Institute (web site: http://www.wicell.org/, Madison, Wis., USA), National Institute of Health, Kyoto University and the like and, for example, can be purchased from Cellartis AB (web site: http://www.cellartis.com/, Sweden) and the like.

As iPS cells, iPS cells derived from any warm-blooded animal, preferably mammal, can be used. Examples of the mammal include mouse, rat, guinea pig, hamster, rabbit, cat, dog, sheep, swine, bovine, horse, goat, monkey and human. Preferable examples of the iPS cells include iPS cells derived from human.

Specific examples of iPS cells include cells that have acquired multipotency like that of ES cells and were obtained by introducing plural genes into somatic cells such as skin cells and the like, for example, iPS cells obtained by introducing Oct3/4 gene, Klf4 gene, C-Myc gene and Sox2 gene, iPS cells obtained by introducing Oct3/4 gene, Klf4 gene and Sox2 gene (Nat Biotechnol 2008; 26: 101-106). In addition, a method wherein transgenes are further reduced (Nature. 2008 Jul. 31; 454(7204):646-50), a method utilizing a low-molecular-weight compound (Cell Stem Cell. 2009 Jan. 9; 4(1):16-9, Cell Stem Cell. 2009 Nov. 6; 5(5):491-503), a method utilizing a transcription factor protein instead of a gene (Cell Stem Cell. 2009 May 8; 4(5):381-4) and the like can be mentioned.

The produced iPS cells can be used for the present invention, irrespective of the production method thereof.

Specific examples of human iPS cell line include 253G1 strain (iPS cell line produced by expressing OCT4/SOX2/KLF4 in skin fibroblast of 36-year-old female), 201B7 strain (iPS cell line produced by expressing OCT4/SOX2/KLF4/c-MYC in skin fibroblast of 36-year-old female), 1503-iPS (297A1) (iPS cell line produced by expressing OCT4/SOX2/KLF4/c-MYC in skin fibroblast of 73-year-old female), 1392-iPS(297F1) (iPS cell line produced by expressing OCT4/SOX2/KLF4/c-MYC in skin fibroblast of 56-year-old male), NHDF-iPS(297L1) (iPS cell line produced by expressing OCT4/SOX2/KLF4/c-MYC in skin fibroblast of newborn boy) and the like.

As the somatic stem cells, one derived from human can be used. Here, the somatic stem cells refers to cells capable of differentiation into pancreatic hormone-producing cells, for example, stem cells present in mesenchymal stem cells derived from bone marrow and fat and stem cells present in the pancreas.

1. Cell Production Method

The production method of the present invention includes a method of producing pancreatic hormone-producing cells from stem cells, endodermal cells or progenitor cells of pancreatic hormone-producing cells, a method of producing endodermal cells from stem cells, and a method of producing progenitor cells of pancreatic hormone-producing cells from endodermal cells. The production method of the present invention also includes a method of inducing differentiation of cells in a less differentiated state into a more differentiated state.

The present invention provides a method of producing pancreatic hormone-producing cells, comprising subjecting stem cells to the following steps (1)-(4):

(1) a step of cultivating stem cells in a medium containing an activator of activin receptor-like kinase-4,7 and a GSK3 inhibitor (2) a step of cultivating the cells obtained in the aforementioned step (1) in a medium containing an activator of activin receptor-like kinase-4,7

(3) a step of cultivating the cells obtained in the aforementioned step (2) in a medium containing any one or more kinds selected from the group consisting of (a) retinoic acid receptor agonists, (b) at least one kind selected from the group consisting of inhibitors of AMP-activated protein kinase and/or activin receptor-like kinase-2,3,6, and BMP antagonists, and (c) inhibitors of activin receptor-like kinase-4,5,7

(4) a step of cultivating the cells obtained in the aforementioned step (3).

In the production method of the present invention (differentiation induction method), stem cells are generally cultured on a culture vessel. Examples of the culture vessel used here include flask, tissue culture flask, dish, petri dish, tissue culture dish, multidish, microplate, microwell plate, multiplate, multiwell plate, chamber slide, Schale, tube, tray, culture bag and roller bottle. Preferred are dish, petri dish, tissue culture dish, multidish, microplate, microwell plate, multiplate, multiwell plate and the like. The culture vessel is preferably applied with a coating suitable for maintaining and cultivating stem cells. Specifically, use of a culture vessel coated with feeder cells or an extracellular substrate component is preferable. While the feeder cells are not particularly limited, for example, fibroblast (mouse embryonic fibroblast (MEF), mouse fibroblast (STO) etc.) can be mentioned. The feeder cells are preferably inactivated by a method known per se, for example, radiation (gamma-ray etc.) irradiation, treatment with anti-cancer agent (mitomycin C etc.) and the like. Examples of the extracellular substrate component include fibrous protein such as gelatin, collagen, elastin and the like, glucosaminoglycan and proteoglycan such as hyaluronic acid, chondroitin sulfate and the like, cell adhesion protein such as fibronectin, vitronectin, laminin and the like, basement membrane component such as Matrigel and the like, and the like.

Step (1): a Step of Cultivating Stem Cells in a Medium Containing an Activator of Activin Receptor-Like Kinase-4,7 and a GSK3 Inhibitor This step corresponds to a step of inducing differentiation of stem cells into endodermal cells, which is performed singly or preferably together with the below-mentioned step (2). In the present invention, therefore, a production method of endodermal cells using stem cells as a starting material can also be provided by this step (1).

The activator of activin receptor-like kinase (ALK)-4,7 used in this step is selected from the substances having an activation action on ALK-4 and/or ALK-7.

Examples of the activator of activin receptor-like kinase-4,7 used in this step include activin, Nodal and Myostatin. Of these, activin is preferable as the activator of activin receptor-like kinase-4,7 used in this step.

The above-mentioned activin is a 24 kD peptidic cell proliferation and differentiation factor belonging to the TGFβ (transforming growth factor β) family, wherein two β subunits constitute a dimer via an SS bond (Ling, N., et al., (1986) Nature 321, 779-782; Vale, W., et al., (1986) Nature 321, 776-779). As activin, activins A, B, C, D and AB are known, and any of the activins A, B, C, D and AB can be used in this step. Activin A is particularly preferably used as the activin to be used for this step. As the activin, moreover, an activin derived from any mammal such as human, mouse etc. can be used. As the activin to be used for this step, an activin derived from the same animal species as the stem cells to be used for differentiation is preferably used. For example, stem cells derived from human are used as a starting material, an activin derived from human is preferably used. These activins are commercially available.

While the concentration of an activator of activin receptor-like kinase-4,7 in the medium in this step is appropriately determined according to the kind of the activator of activin receptor-like kinase-4,7, the concentration of human activin A used as an activator of activin receptor-like kinase-4,7 is generally 0.1-200 ng/ml, preferably 5-150 ng/ml, particularly preferably 10-100 ng/ml.

This step is characterized by the use of a medium containing a GSK3 inhibitor together with an activator (preferably activin A) of activin receptor-like kinase-4,7. When stem cells are cultured in the presence of an activator of activin receptor-like kinase-4,7 and a GSK3 inhibitor, it can be more preferably differentiated into endodermal cells.

In the present specification, the substance includes low-molecular-weight compound, peptide, protein and the like.

The GSK3 inhibitor to be used in this step is selected from the group consisting of substances having a GSK3a inhibitory activity, substances having a GSK3β inhibitory activity, and substances having a GSK3a inhibitory activity and a GSK3β inhibitory activity in combination. As a GSK3 inhibitor to be used in this step, a substance having a GSK3β inhibitory activity or a substance having a GSK3α inhibitory activity and a GSK3β inhibitory activity in combination is preferable.

Specific examples of the above-mentioned GSK3 inhibitor include CHIR98014, CHIR99021, Kenpaullone, AR-AO144-18, TDZD-8, SB216763, BIO, TWS-119, SB415286 and the like. These can be purchased from Axon Medchem BV, Wako Pure Chemical Industries, Ltd., Enzo Life Sciences, Inc., Merck Biosciences, Tocris bioscience, Stemgent, Sigma and the like, where the same name and the same trade name refer to the same substance, and the structure and the property are the same irrespective of the manufacturer. Even when they are not available as commercial products, those of ordinary skill in the art can prepare them according to a known document.

In addition, antisense oligonucleotide, siRNA and the like for GSK3 mRNA can also be used as GSK3 inhibitors. All of these are commercially available or can be synthesize according to published documents.

The above-mentioned GSK3 inhibitor is preferably CHIR99021 (6-[[2-[[4-(2,4-dichlorophenyl)-5-(4-methyl-1H-imidazol-2-yl)-2-pyrimidinyl]amino]ethyl]amino]nicotinonitrile), SB216763 (3-(2,3-dichlorophenyl)-4-(1-methyl-1H-indol-3-yl)-1H-pyrrole-2,5-dione), or SB415286 (3-[(3-chloro-4-hydroxyphenyl)amino]-4-(2-nitrophenyl)-1H-pyrrole-2,5-dione).

In this step, CHIR99021 (6-[[2-[[4-(2,4-dichlorophenyl)-5-(4-methyl-1H-imidazol-2-yl)-2-pyrimidinyl]amino]ethyl]amino]nicotinonitrile), which is a GSK3 inhibitor, is preferably used.

While the concentration of a GSK3 inhibitor in the medium is appropriately determined according to the kind of the GSK3 inhibitor to be used, the concentration of CHIR99021 when used as a GSK3 inhibitor is generally 0.1-20 μM, preferably 1-5 μM. The concentration of SB415286 when used as a GSK3 inhibitor is generally 0.1-20 μM, preferably 1-10 μM. The concentration of SB216763 when used as a GSK3 inhibitor is generally 0.1-30 μM, preferably 0.5-20 μM.

In this step, an activator of activin receptor-like kinase-4,7 and a GSK3 inhibitor may be simultaneously added to the medium, or may be individually added to the medium in a staggered manner, as long as differentiation of stem cells into endodermal cells can be induced. It is convenient and preferable that an activator of activin receptor-like kinase-4,7 and a GSK3 inhibitor be simultaneously added to a medium.

The medium to be used in this step is not particularly limited as long as it contains, as mentioned above, an activator of activin receptor-like kinase-4,7 and a GSK3 inhibitor, and is generally, a medium used for cultivating stem cells (hereinafter sometimes to be referred to as a basal medium), which is added with an activator of activin receptor-like kinase-4,7 and a GSK3 inhibitor.

The above-mentioned basal medium is not particularly limited as long as it can be used for culturing animal cells, such as BME medium, BGJb medium, CMRL 1066 medium, Glasgow MEM medium, Improved MEM Zinc Option medium, IMDM medium, Medium 199 medium, Eagle MEM medium, αMEM medium, DMEM medium, ham medium, RPMI 1640 medium, Fischer's medium, and mixed medium thereof and the like. These basal media can be purchased from Invitrogen, SIGMA, Wako Pure Chemical Industries, Ltd., Dainippon Sumitomo Pharma Co., Ltd. and the like. Media with the same name or same trade name are equal in the composition irrespective of the manufacturer. The basal medium to be used in this step is preferably RPMI 1640 medium and Improved MEM Zinc Option medium.

The medium to be used in this step may be a serum-containing medium or a serum-free medium. Here, the serum-free medium means a basal medium free of unadjusted or unpurified serum, and a medium contaminated with purified blood-derived component or animal tissue-derived component (e.g., growth factor) is considered to fall under a serum-free medium. When the medium to be used in this step is a serum-containing medium, a serum of a mammal such as fetal bovine serum and the like can be used. The concentration of the serum in the medium is generally 0.01-20 wt %, preferably 0.1-10 wt %.

The medium to be used in this step may also contain a serum replacement. Examples of the serum replacement include albumin (e.g., lipid rich albumin), transferrin, fatty acid, collagen precursor, trace element (e.g., zinc, selenium), B-27% supplement, N2 supplement, knockout serum replacement, 2-mercaptoethanol, 3' thiolglycerol, or equivalents thereof. The concentration thereof in the medium is the same as the concentration of the aforementioned serum in the medium.

A knockout serum replacement can be purchased from Invitrogen. Other serum replacements can be purchased from Invitrogen, SIGMA, Wako Pure Chemical Industries, Ltd., Dainippon Sumitomo Pharma Co., Ltd. and the like. Reagents and additives with the same name or same trade name are equal in the composition irrespective of the manufacturer.

The medium to be used in this step may also contain lipid, amino acid (e.g., non-essential amino acid), vitamin, growth factor, cytokine, antioxidant, 2-mercaptoethanol, pyruvic acid, buffering agent, inorganic salts, antibiotic (e.g., penicillin, streptomycin) or antibacterial agent (e.g., amphotericin B) and the like. The concentration thereof in the medium is the same as the concentration of the aforementioned serum in the medium.

This step is performed by cultivation at a culture temperature suitable for culture of the stem cells to be used (generally 30-40° C., preferably about 37° C.) for 6-60 hr (preferably 12-36 hr), in a $CO_2$ incubator aerated with 1-100 (preferably 5%) of carbon dioxide.

Step (2): a Step of Cultivating the Cells Obtained in the Aforementioned Step (1) in a Medium Containing an Activator of Activin Receptor-Like Kinase-4,7

This step is performed following the above-mentioned step (1), and corresponds to a step for completing differentiation induction of stem cells into endodermal cells.

That is, it is a step of cultivating the cells obtained in the aforementioned step (1) in a medium containing an activator of activin receptor-like kinase-4,7.

Specifically, after cultivating stem cells in a medium containing an activator of activin receptor-like kinase-4,7 and a GSK3 inhibitor (step (1)), the medium is changed to a medium containing an activator of activin receptor-like kinase-4,7.

The medium to be used in this step is prepared by adding an activator of activin receptor-like kinase-4,7 to a basal medium exemplified in the aforementioned step (1) (when desired, optionally containing various additives exemplified in the aforementioned step (1), serum or serum replacement). In addition, when desired, a GSK3 inhibitor exemplified in the aforementioned step (1) may be contained in the medium.

While the medium to be used in this step may be prepared using the same kind of basal medium as the basal medium used in the aforementioned step (1) or one prepared using a different basal medium, it is preferably prepared using the same kind of basal medium.

Examples of the activator of activin receptor-like kinase-4,7 to be used in this step include those exemplified in the aforementioned step (1).

When activin is used as an activator of activin receptor-like kinase-4,7 in this step, the activin may be any of activins A, B, C, D and AB, and activin A is preferable. The activin may be derived from any animal species such as human, mouse and the like. As the activin, moreover, an activin derived from any mammal such as human, mouse etc. can be used. As the activin to be used for this step, an activin derived from the same animal species as the stem cells to be a starting material is preferably used. For example, when stem cells derived from human are used as a starting material, human activin is preferably used. These activins are commercially available.

While the concentration of an activator of activin receptor-like kinase-4,7 in the medium in this step is appropriately determined according to the kind of the activator of activin receptor-like kinase-4,7 to be used, the concentration of human activin A when used as an activator of activin receptor-like kinase-4,7 is generally 0.1-200 ng/ml, preferably 5-150 ng/ml, particularly preferably 10-100 ng/ml.

This step is performed by cultivation at a culture temperature suitable for culture of the stem cells to be used (generally 30-40° C., preferably about 37° C.) for 6-144 hr (preferably 12-72 hr), in a $CO_2$ incubator aerated with 1-100 (preferably 5%) of carbon dioxide.

In this step, differentiation of stem cells into endoderm cells can be confirmed by evaluating variation in the expression of protein and gene that show endodermal cell-specific expression (the above-mentioned protein and gene are sometimes to be referred to as endodermal markers in the present specification). The variation in the expression of the above-mentioned endodermal markers can be evaluated by, for example, an evaluation method of protein expression, utilizing an antigen-antibody reaction, an evaluation method of gene expression, utilizing quantitative RT-PCR and the like. Examples of the above-mentioned endodermal marker include SOX17 (sex determining region Y), Goosecoid (goosecoid homeobox), CXCR4 (chemokine (C—X—C motif) receptor 4), and FOXA2 (forkhead box A2).

Step (3): a Step of Cultivating the Cells Obtained in the Aforementioned Step (2) in a Medium Containing any One or More Kinds Selected from the Group Consisting of (a) Retinoic Acid Receptor Agonists, (b) at Least One Kind Selected from the Group Consisting of Inhibitors of AMP-Activated Protein Kinase and/or activin receptor-like kinase-2,3,6, and BMP antagonists, and (c) Inhibitors of Activin Receptor-Like Kinase-4,5,7

This step corresponds to a step of inducing differentiation of an endodermal cells obtained via the above-mentioned steps (1) and (2) into progenitor cells of pancreatic hormone-producing cells.

The retinoic acid receptor (RAR) agonist to be used in this step may be a naturally-occurring retinoid, or chemically synthesized retinoid, a retinoic acid receptor agonist compound free of retinoid skeleton, or a naturally-occurring substance having a retinoic acid receptor agonist activity. Examples of the natural retinoid having a RAR agonist activity include retinoic acid (stereoisomers of all-trans retinoic acid (all-trans RA) and 9-cis-retinoic acid (9-cis RA) are known). A chemically synthesized retinoid is known in this field (U.S. Pat. Nos. 5,234,926, 4,326,055 etc.). Examples of the retinoic acid receptor agonist compound free of retinoid skeleton include Am80, AM580, TTNPB and AC55649. Examples of the naturally-occurring substance having a retinoic acid receptor agonist activity include honokiol and magnolol (Annual Report of Research Institute for Biological Function 9:55-61, 2009). The RAR agonist to be used in this step is preferably retinoic acid, AM580 (4-[[5,6,7,8-tetrahydro-5,5,8,8-tetramethyl-2-naphthalenyl]carboxamide]benzoic acid), TTNPB (4-[[E]-2-[5,6,7,8-tetrahydro-5,5,8,8-tetramethyl-2-naphthalenyl]-1-propenyl]benzoic acid), AC55649 (4'-octyl-[1,1'-biphenyl]-4-carboxylic acid), more preferably retinoic acid. While the concentration of an RAR agonist in the medium is appropriately determined according to the kind of the RAR agonist to be used, the concentration of retinoic acid when used as an RAR agonist is generally 0.1-100 μM, preferably 0.5-10 μM. The concentration of TTNPB when used as an RAR agonist is generally 0.02-20 μM, preferably 0.05-10 μM. The concentration of AM580 when used as an RAR agonist is generally 0.02-20 μM, preferably 0.05-10 μM. The concentration of AC55649 when used as an RAR agonist is generally 0.02-20 μM, preferably 0.1-10 μM.

The inhibitor of AMP-activated protein kinase and/or activin receptor-like kinase-2,3,6 to be used in this step is not particularly limited as long as it is a substance having an inhibitory activity of AMP-activated protein kinase and/or activin receptor-like kinase-2,3,6 (e.g., a compound having an inhibitory activity of AMP-activated protein kinase and/or activin receptor-like kinase-2,3,6, antisense oligonucleotide and siRNA of mRNA for AMP-activated protein kinase and/or activin receptor-like kinase-2,3,6). In addition to a synthesizable (low molecular) compound, various physiologically active substances such as cytokine and the like can also be preferably used as long as they possess the activity. Preferable examples of the substance having an inhibitory activity of AMP-activated protein kinase and/or activin receptor-like kinase-2,3,6 include a compound having an inhibitory activity of AMP-activated protein kinase and/or activin receptor-like kinase-2,3,6. The compound is selected from the group consisting of compounds having inhibitory activity on AMP-activated protein kinase (AMPK), compounds having inhibitory activity on activin receptor-like kinase (ALK)-2,3,6, and compounds having inhibitory activity on AMP-activated protein kinase and inhibitory activity on activin receptor-like kinase-2,3,6 in combination.

Here, an inhibitor of activin receptor-like kinase (ALK)-2, 3,6 or a substance having an inhibitory activity on ALK-2,3,6 means a compound or substance having an inhibitory activity on at least one kind of ALK selected from ALK-2, ALK-3 and ALK-6.

Examples of the compound having AMPK inhibitory activity include dorsomorphin (6-[4-(2-piperidin-1-ylethoxy)phenyl]-3-pyridin-4-ylpyrazolo[1,5-a]pyrimidine), araA (adenine-9-β-d-arabino furanoside), C75 and the like. As the activin receptor-like kinase (ALK), ALK-2,3,6, which is a 1-type receptor of BMP (Bone Morphogenetic Protein), the below-mentioned TGF-β, Activin, ALK-4,5,7, which is a 1-type receptor of Nodal, and the like are known. As a compound having ALK-2,3,6 inhibitory activity, dorsomorphin, LDN-193189 and the like can be mentioned. Dorsomorphin has both AMPK inhibitory activity and ALK-2,3,6 inhibitory activity. As an inhibitor of AMP-activated protein kinase and/or activin receptor-like kinase-2,3,6, dorsomorphin is preferable.

BMP antagonist to be used in this step is not particularly limited as long as it is a substance that inhibits the function BMP has (i.e., activation of signal via activin receptor-like kinase-2,3,6) (e.g., protein that inhibits the function BMP has by binding to BMP (Trends Cell Biol. 20 (2001) 244-256), antisense oligonucleotide and siRNA of mRNA for the protein). Examples of the BMP antagonist to be used in this step include Noggin.

These compounds can be purchased from SIGMA, Tocris bioscience, Stemgent, Merck Biosciences and the like. Compounds with the same name and the same trade name refer to the same compound, and they are equal in the structure and the property irrespective of the manufacturer. When they are not available as commercial products, those of ordinary skill in the art can prepare them according to known documents.

In addition, antisense oligonucleotide and siRNA of mRNA for AMP-activated protein kinase and/or ALK-2,3,6 and the like can also be used as an inhibitor of AMP-activated protein kinase and/or ALK-2,3,6. In this step, moreover, when an increase of a differentiation factor belonging to the BMP family or secretion of the differentiation factor, from the cells under culture into the medium, is confirmed, an antibody that neutralizes the activity of the differentiation factor, or Noggin, Chordin, Cerberus, Gremlin and the like, which are known to bind to BMP to inhibit its action, can also be used as an inhibitor of AMP-activated protein kinase and/or ALK-2, 3,6.

In this step, moreover, when an increase of a differentiation factor belonging to the activin family or secretion of the differentiation factor, from the cells under culture into the medium, as exemplified in (1), is confirmed, an antibody that neutralizes the activity of the differentiation factor, or follistatin known to bind to activin to inhibit its action, can also be used as an inhibitor of AMP-activated protein kinase and/or ALK-2,3,6.

While the concentration of an inhibitor of AMP-activated protein kinase and/or activin receptor-like kinase-2,3,6 in the medium when the inhibitor is used in this step is appropriately determined according to the kind of the inhibitor to be used, the concentration of dorsomorphin when it is used therefor is generally 0.1-20 μM, preferably 0.2-5 μM.

While the concentration of BMP antagonist when it is used in this step is appropriately determined according to the kind of the BMP antagonist to be used, the concentration of Noggin when it is used therefor is generally 1 ng/ml-1000 ng/ml, preferably 20 ng/ml-500 ng/ml.

An inhibitor of activin receptor-like kinase (ALK)-4,5,7 is selected from the compounds having an inhibitory activity on at least one kind of ALK selected from ALK-4, ALK-5 and ALK-7.

As the inhibitor of ALK-4,5,7 to be used in this step, SB-431542, SB-505124, SB-525334, A-83-01, GW6604, LY580276, ALK5 inhibitor II, TGFβRI kinase inhibitor VIII, SD-208 and the like can be mentioned.

These can be purchased from SIGMA, Tocris bioscience, Wako Pure Chemical Industries, Ltd. and the like. Compounds with the same name and the same trade name refer to the same compound, and they are equal in the structure and the property irrespective of the manufacturer. When they are not available as commercial products, those of ordinary skill in the art can prepare them according to known documents.

In addition, antisense oligonucleotide and siRNA of mRNA for ALK-4,5,7 can also be used as an ALK-4,5,7 inhibitor.

As the inhibitor of ALK-4,5,7 to be used in this step, SB-431542 (4-[4-(1,3-benzodioxol-5-yl)-5-(2-pyridinyl)-1H-imidazol-2-yl]-benzamide or hydrate thereof), A-83-01 (3-[6-methyl-2-pyridinyl]-N-phenyl-4-[4-quinolinyl]-1H-pyrazole-1-carbothioamide), ALK5 inhibitor II (2-[3-[6-methylpyridin-2-yl]-1H-pyrazol-4-yl]-1,5-naphthyridine), and TGFβRI kinase inhibitor VIII (6-[2-tert-butyl-5-[6-methylpyridin-2-yl]-1H-imidazol-4-yl]-quinoxaline) are preferable, and SB-431542 (4-[4-(1,3-benzodioxol-5-yl)-5-(2-pyridinyl)-1H-imidazol-2-yl]-benzamide or hydrate thereof) is more preferable. While the concentration of an inhibitor of activin receptor-like kinase-4,5,7 in the medium is appropriately determined according to the kind of the inhibitor to be used, the concentration of SB-431542 when used as an inhibitor of activin receptor-like kinase-4,5,7 is generally, 0.1-50 μM, preferably 1-20 μM. The concentration of ALK5 inhibitor II when used as an inhibitor of activin receptor-like kinase-4,5,7 is generally 0.05-50 μM, preferably 0.2-10 μM. The concentration of A-83-01 when used as an inhibitor of activin receptor-like kinase-4,5,7 is generally 0.05-50 μM, preferably 0.1-10 μM. The concentration of TGFβRI kinase inhibitor VIII when used as an inhibitor of activin receptor-like kinase-4,5,7 is generally 0.05-50 μM, preferably 0.1-10 μM.

Step (3) is preferably performed in a medium containing all 3 kinds of components of (a) a retinoic acid receptor agonist, (b) at least one kind selected from the group consisting of inhibitors of AMP-activated protein kinase and/or activin receptor-like kinase-2,3,6, and BMP antagonists, and (c) an inhibitor of activin receptor-like kinase-4,5,7, preferably performed in a medium containing all 3 kinds of a retinoic acid receptor agonist, an inhibitor of AMP-activated protein kinase and/or activin receptor-like kinase-2,3,6, and an inhibitor of activin receptor-like kinase-4,5,7, more preferably performed in a medium containing retinoic acid, dorsomorphin, and 4-[4-(1,3-benzodioxol-5-yl)-5-(2-pyridinyl)-1H-imidazol-2-yl]-benzamide or hydrate thereof, and particularly preferably performed in a medium containing retinoic acid, dorsomorphin, and 4-[4-(1,3-benzodioxol-5-yl)-5-(2-pyridinyl)-1H-imidazol-2-yl]-benzamide or hydrate thereof.

In this step, when two or more kinds of (a) a retinoic acid receptor agonist, (b) at least one kind selected from the group consisting of inhibitors of AMP-activated protein kinase and/or activin receptor-like kinase-2,3,6, and BMP antagonists, and (c) an inhibitor of activin receptor-like kinase-4,5,7 are used in combination, they may be simultaneously added to the medium, or may be individually added to the medium in a staggered manner, as long as differentiation into progenitor cells of pancreatic hormone-producing cells can be induced. While it can be appropriately determined depending on the of kind of each factor, it is convenient and preferable that (a) a retinoic acid receptor agonist, (b) at least one kind selected from the group consisting of inhibitors of AMP-activated protein kinase and/or activin receptor-like kinase-2,3,6, and BMP antagonists, and (c) an inhibitor of activin receptor-like kinase-4,5,7 be simultaneously added to a medium.

The medium to be used in this step is prepared by adding one or more kinds selected from the group consisting of (a) retinoic acid receptor agonists, (b) at least one kind selected from the group consisting of inhibitors of AMP-activated protein kinase and/or activin receptor-like kinase-2,3,6, and BMP antagonists, and (c) inhibitors of activin receptor-like kinase-4,5,7, to the basal medium exemplified in the aforementioned step (1) (when desired, it may contain various additives exemplified in the aforementioned step (1), serum or serum replacement). The medium to be used in this step may be prepared by using the same kind of a basal medium as the above-mentioned step (1) and step (2), or using a different basal medium. Since induction of differentiation into progenitor cells of pancreatic hormone-producing cells can be performed more efficiently, Improved MEM Zinc Option medium (Invitrogen) is preferably used as the basal medium for this step. The medium can also be prepared according to a known document (Richter A. et al., National Cancer (1972) 49, 1705). Furthermore, B-27 supplement (Brewer G. J. et al., J. Neurosci. Res. (1993) 35, 567) as a serum replacement can also be preferably added to the medium.

The concentration of B-27 supplement in the medium is 0.01-10 wt %, preferably 0.1-2 wt %.

This step is performed by cultivation at a culture temperature suitable for culture of the stem cells or endodermal cells to be used (generally 30-40° C., preferably about 37° C.) for 72-288 hr (preferably 120-216 hr), in a $CO_2$ incubator aerated with 1-10% (preferably 5%) of carbon dioxide.

In this step, differentiation induction of endoderm cells into progenitor cells of pancreatic hormone-producing cells can be confirmed by evaluating variation in the expression of protein and gene that show progenitor cells of pancreatic hormone-producing cells-specific expression (the above-mentioned protein and gene are sometimes to be referred to as progenitor cells of pancreatic hormone-producing cells marker in the present specification). The variation in the expression of the above-mentioned progenitor cells of pancreatic hormone-producing cells marker can be evaluated by, for example, an evaluation method of protein expression, utilizing an antigen-antibody reaction, an evaluation method of gene expression, utilizing quantitative RT-PCR and the like. Examples of the above-mentioned progenitor cells of pancreatic hormone-producing cells marker include NGN3, HNF6 (hepatocyte nuclear factor 6, aka: one cut homeobox 1), PDX1 (pancreatic and duodenal homeobox 1) and the like.

Using this step (3), progenitor cells of pancreatic hormone-producing cells can also be produced efficiency using an endodermal cells other than the endodermal cells obtained via the above-mentioned steps (1) and (2) or stem cells as a starting material. In the present invention, therefore, a production method of progenitor cells of pancreatic hormone-producing cells by using endodermal cells or stem cells as a starting material by this step (3), that is, a production method of progenitor cells of pancreatic hormone-producing cells, comprising cultivating endodermal cells or stem cells in a medium containing one or more kinds selected from the group consisting of the following (a)-(c), more preferably all of the following (a)-(c), can also be provided:

(a) the above-mentioned retinoic acid receptor agonist
(b) the above-mentioned at least one kind selected from the group consisting of inhibitors of AMP-activated protein kinase and/or activin receptor-like kinase-2,3,6, and BMP antagonists
(c) the above-mentioned inhibitor of activin receptor-like kinase-4,5,7.

Also, in a production method of progenitor cells of pancreatic hormone-producing cells using, as a starting material, endodermal cells other than the endodermal cells obtained via the above-mentioned steps (1) and (2) or stem cells, the concentration, in each of the above-mentioned (a)-(c), in the medium, basal medium to be used for culture, and cell culture conditions (temperature, time and the like) can be similar to those in step (3) in a production method of progenitor cells of pancreatic hormone-producing cells using endodermal cells obtained via the above-mentioned steps (1) and (2) or stem cells as a starting material.

Step (4): a Step of Cultivating the Cells Obtained in the Aforementioned Step (3).

This step corresponds to a step of inducing differentiation of progenitor cells of pancreatic hormone-producing cells into pancreatic hormone-producing cells.

The basal medium to be used in this step may be one exemplified in the aforementioned step (1). The basal medium to be used in this step may be prepared by using the same kind of a basal medium in the above-mentioned steps (1)-(3), or using a different basal medium. Since induction of differentiation into pancreatic hormone-producing cells can be performed more efficiently, Improved MEM Zinc Option medium (Invitrogen) is preferably used as the basal medium for this step. The medium can also be prepared according to a known document (Richter A. et al., National Cancer (1972) 49, 1705). Particularly, Improved MEM Zinc Option medium (Invitrogen) added with B-27 supplement is preferably used. The concentration of the B-27 supplement in the medium is 0.01-10 wt %, preferably 0.1-2 wt %. In addition, an additive to improve cells survival rate may be added to the Improved MEM Zinc Option medium. Examples of such additive include fetal bovine serum, serum replacements such as knockout serum replacement, N2 supplement and the like, and the like. The concentration of the aforementioned additive in the medium is 0.01-10 wt %, preferably 0.1-2 wt %.

In another more preferable embodiment in this step, a medium added with at least one kind selected from the group consisting of (i) at least one kind selected from the group consisting of adenylate cyclase activators, cAMP phosphodiesterase inhibitors and cAMP analogs, (ii) steroids and (iii) inhibitors of activin receptor-like kinase-4,5,7 (ALK-4,5,7) is used. When desired, a medium further added with nicotinamide can also be used.

Examples of (i) adenylate cyclase activators, cAMP phosphodiesterase inhibitors and cAMP analogs to be used in this step include a compound having an adenylate cyclase activity, a compound having a cAMP phosphodiesterase inhibitory activity, a compound having both an adenylate cyclase activity and a cAMP phosphodiesterase inhibitory activity and the like. More specifically, forskolin, dibutyl cAMP, PACAP27 (pituitary adenylate cyclase activating polypeptide 27), IBMX (3-isobutyl-1-methylxanthine) and the like can be mentioned. Of these, forskolin is preferably used. The concentration of (i) at least one kind selected from the group consisting of adenylate cyclase activators, cAMP phosphodiesterase inhibitors and cAMP analogs to be used in this step in the medium is appropriately determined according to the kind of the adenylate cyclase activator, cAMP phosphodiesterase inhibitor and cAMP analog to be used. The concentration of forskolin when used therefor is generally 0.1-50 μM, preferably 2-50 μM, the concentration of IBMX when used therefor is generally 5-1000 μM, preferably 50-500 μM, and the concentration of dibutyl cAMP when used therefor is generally 10-4000 μM, preferably 100-1000 μM.

The (ii) steroid to be used in this step is not particularly limited as long as it can contribute to the induction of cell differentiation. Examples of the (ii) steroid to be used in this step include dexamethasone, hydrocortisone, betamethasone and beclomethasone. Of these, dexamethasone is preferably used. The concentration of steroid in the medium is appropriately determined according to the kind of the steroid to be used. The concentration of dexamethasone when used as steroid is generally 0.1-50 μM, preferably 2-50 μM. The concentration of hydrocortisone when used as a steroid is generally 0.1-100 μM, preferably 1-50 μM. The concentration of betamethasone when used as a steroid is generally 0.1-50 μM, preferably 0.5-20 μM. The concentration of beclomethasone when used as a steroid is generally 0.1-50 μM, preferably 0.2-20 μM.

The (iii) inhibitor of activin receptor-like kinase (ALK)-4, 5,7 to be used in this step is selected from the compounds having an inhibitory activity on at least one kind of ALK selected from ALK-4, ALK-5 and ALK-7. As the (iii) inhibitor of activin receptor-like kinase (ALK)-4,5,7 to be used in this step, a compound that inhibits the activity of ALK-4,5,7 can be mentioned, which specifically includes 2-(3-(6-methylpyridin-2-yl)-1H-pyrazol-4-yl)-1,5-naphthyridine (ALK5 inhibitor II), ALK5 inhibitor I, ALK5 inhibitor VII, SB-431542, SB-505124, SB-525334, A-83-01, GW6604, LY580276, TGFβRI kinase inhibitor VIII, SD-208 and the like. Of these, ALK5 inhibitor II, SB-431542, A-83-01 and TGFβRI kinase inhibitor VIII (6-[2-tert-butyl-5-[6-methylpyridin-2-yl]-1H-imidazol-4-yl]-quinoxaline) are preferable, and ALK5 inhibitor II is particularly preferable. While the concentration of an ALK-4,5,7 inhibitor in the medium is appropriately determined according to the kind of the ALK-4,5,7 inhibitor to be used, the concentration of ALK5 inhibitor II when used as an ALK-4,5,7 inhibitor is generally 0.1-50 μM, preferably 1-20 μM. The concentration of A-83-01 when used as an ALK-4,5,7 inhibitor is generally 0.1-50 μM, preferably 0.1-10 μM. The concentration of SB-431542 when used as an ALK-4,5,7 inhibitor is generally 0.1-50 μM, preferably 1-20 μM. The concentration of TGFβRI kinase inhibitor VIII when used as an ALK-4,5,7 inhibitor is generally 0.1-50 μM, preferably 0.5-10 μM.

In this step, nicotinamide (also called niacin or nicotinic acid amide) can be added to the medium when desired. Nicotinamide has been reported to suppress the cell death of pancreatic β cells due to its function as a poly-ADP ribose synthesis inhibitor. The concentration of nicotinamide in the medium is generally 0.1-20 mM, preferably 5-20 mM.

The aforementioned (i) at least one kind selected from the group consisting of adenylate cyclase activators, cAMP phosphodiesterase inhibitors and cAMP analogs, (ii) steroid and (iii) an inhibitor of activin receptor-like kinase-4,5,7 (ALK-4,5,7) can be purchased from SIGMA, Enzo Life Sciences, Inc., Merck Biosciences and the like. Those with the same name and the same trade name refer to the same compound, and they are equal in the structure and the property irrespective of the manufacturer. When they are not available as commercial products, they can be prepared according to known documents.

The medium to be used in this step is prepared by adding, to a basal medium, any one or more kinds of components selected from the group consisting of (i) at least one kind selected from the group consisting of adenylate cyclase activators, cAMP phosphodiesterase inhibitors and cAMP analogs, (ii) steroids, and (iii) inhibitors of ALK-4,5,7. When desired, the medium may contain nicotinamide in addition to the above-mentioned one or more kinds of components. The above-mentioned one or more kinds of components and nicotinamide are used in combination, they may be simultaneously added to the medium, or may be individually added to the medium in a staggered manner, as long as differentiation into pancreatic hormone-producing cells can be induced. It is convenient and preferable that the above-mentioned one or more kinds of components and/or nicotinamide be simultaneously added to a medium.

This step is performed by cultivation at a culture temperature (generally 30-40° C., preferably about 37° C.) suitable for culturing progenitor cells of pancreatic hormone-producing cells to be used for 24-240 hr (preferably 72-192 hr), in a $CO_2$ incubator aerated with 1-10% (preferably 5%) of carbon dioxide.

In this step, differentiation induction of progenitor cells of pancreatic hormone-producing cells into pancreatic hormone-producing cells can be confirmed by evaluating variation in the expression of protein and gene that show pancreatic hormone-producing cells-specific expression (the above-mentioned protein and gene are sometimes to be referred to as pancreatic hormone-producing cells marker in the present specification) or measuring the amount of pancreatic hormone secreted in the medium. The variation in the expression of the above-mentioned pancreatic hormone-producing cells marker can be evaluated by, for example, an evaluation method of protein expression, utilizing an antigen-antibody reaction, an evaluation method of gene expression, utilizing quantitative RT-PCR and the like. The amount of pancreatic hormone secreted in the above-mentioned medium can be measured by a method such as Western blotting analysis, ELISA method and the like or a method analogous thereto, and the like. Examples of the above-mentioned pancreatic hormone-producing cells marker include insulin, glucagon, pancreatic polypeptide, somatostatin, PCSK1 (proprotein convertase subtilisin/kexin type 1), SUR1 (sulfonylurea receptor 1, aka: ATP-binding cassette, sub-family C(CFTR/MRP), member 8), NKX6.1 (NK6 homeobox 1), PAX6 (paired box 6), NEUROD (neurogenic differentiation 1), ARX (aristaless related homeobox) and the like.

As mentioned above, the present invention provides a method of producing pancreatic hormone-producing cells from stem cells. By a similar method, i.e., a method of inducing differentiation of a cell in a less differentiated state into a more differentiated state, differentiations of a stem cell into a cell in various differentiated states (endodermal cell, pancreatic duct cell, pancreatic endocrine cell, pancreatic exocrine cell, cell progenitor common thereto etc.) can be induced. The level of induced differentiation can be known by confirming the presence or absence of expression of a protein or gene that expresses specifically to each cell.

Using the production method of the present invention, differentiation of a stem cell into pancreatic hormone-producing cells can be efficiently induced, whereby pancreatic hormone-producing cells having high pancreatic hormone secretion capability can be supplied in large amounts. The pancreatic hormone-producing cells can be utilized as a tool for developing a medicament (particularly a medicament for cell therapy) or a therapeutic drug for diabetes.

2. Medicament Comprising Cell

The present invention provides a medicament comprising pancreatic hormone-producing cells or progenitor cells of pancreatic hormone-producing cells produced by the above-mentioned production method of the present invention (sometimes to be abbreviated as a medicament of the present invention in the present specification).

Here, the pancreatic hormone-producing cells or progenitor cells of pancreatic hormone-producing cells are not particularly limited as long as it is a cell obtained by the above-mentioned production method of the pancreatic hormone-producing cells or the production method of the progenitor cells of pancreatic hormone-producing cells of the present invention.

In the medicament, the pancreatic hormone-producing cells or progenitor cells of pancreatic hormone-producing cells are used as they are, or a cell mass such as concentrated pellets and the like, by filter filtration and the like, and the like. Furthermore, the medicament added with a protectant such as DMSO (dimethyl sulfoxide) and the like can also be cryopreserved. For safer utilization as the medicament, the medicament may be subjected to a treatment such as heat treatment, radiation treatment and the like, under the conditions that denature the pathogenic protein while maintaining its function as pancreatic hormone-producing cells or function as progenitor cells of pancreatic hormone-producing cells. To prevent growth of pancreatic hormone-producing cells or progenitor cells of pancreatic hormone-producing cells in an amount more than necessary, the cells may be subjected to a treatment in combination with the above-mentioned treatments, such as growth suppression by pre-treatment with mitomycin C and the like, a method including introducing a metabolic enzyme gene naturally absent in mammals into the cells, administering, where necessary, a non-active drug to allow the drug to change to a toxin only in the cells introduced with the metabolism enzyme gene naturally absent in mammals to cause death of the cells (suicide gene therapy) and the like.

The medicament of the present invention is safe and low toxic, and can be administered to a mammal (e.g., human, mouse, rat, guinea pig, swine, monkey).

Examples of the administration mode (transplantation method) of the medicament of the present invention to human include a method containing forming a small incision in the right lower quadrant of human patient, exposing a small mesenteric blood vessel and transplanting cells by inserting a catheter under direct vision; a method containing identifying the portal vein of the liver by echography, and transplanting cells by puncturing a catheter; and a method containing transplanting to the spleen by directly puncturing the spleen under abdominal echo guidance (see Nagata H, Ito M, Shirota C, Edge A, McCowan T C, Fox I J: Route of hepatocyte delivery affects hepatocyte engraftment in the spleen. Transplantation, 76(4):732-4, 2003). Of these, the method of cell transplantation using echography is preferable since it is less invasive, and a specific example of such method is a method containing transplanting to the spleen or liver by directly puncturing under abdominal echo guidance. The dose (amount to be transplanted) of the medicament of the present invention is, for example, $1 \times 10^8$-$1 \times 10^{10}$ cells/individual, preferably, $5 \times 10^8$-$1 \times 10^{10}$ cells/individual, more preferably, $1 \times 10^9$-$1 \times 10^{10}$ cells/individual. For the medicament of the present invention, pancreatic hormone-producing cells prepared using a patient's own cell or a cell of a donor showing cytocompatibility or histocompatibility type tolerable for the patient are preferably used. When sufficient cells cannot be achieved due to the age, constitution and the like, transplantation is also possible by embedding the cell in a capsule such as polyethylene glycol and silicon, a porous container and the like to avoid rejection. In this case, intraperitoneal or subcutaneous transplantation is also possible. The dose (amount to be transplanted) of the medicament of the present invention can be appropriately changed according to the age, body weight, symptom and the like of the patients who receive the administration.

Of the medicaments of the present invention, a medicament comprising pancreatic hormone-producing cells enables production (secretion) of a pancreatic hormone in the body of patient by administration (transplantation) thereof, and is useful for the treatment of a disease caused by a decreased production (secretion) of the pancreatic hormone. For example, a medicament comprising insulin-producing cells is useful for the treatment of diabetes. On the other hand, of the medicaments of the present invention, a medicament comprising progenitor cells of pancreatic hormone-producing cells is, after administration (transplantation) to patient, induced under suitable conditions to differentiate into pancreatic hormone-producing cells, whereby a pancreatic hormone is produced (secreted). Examples of the suitable conditions include a method containing forming a small incision in the right lower quadrant of human patient, exposing a small mesenteric blood vessel and transplanting cells by inserting a catheter under direct vision; a method containing identifying the portal vein of the liver by echography, and transplanting cells by puncturing a catheter; and a method containing transplanting to the spleen by directly puncturing the spleen under abdominal echo guidance (see Nagata H, Ito M, Shirota C, Edge A, McCowan T C, Fox I J: Route of hepatocyte delivery affects hepatocyte engraftment in the spleen. Transplantation, 76(4):732-4, 2003). Of these, the method of cell transplantation using echography is preferable since it is less invasive, and a specific example of such method is a method containing transplanting to the spleen or liver by directly puncturing under abdominal echo guidance. The dose (amount to be transplanted) of the medicament of the present invention is, for example, $1 \times 10^8$-$1 \times 10^{10}$ cells/individual, preferably, $5 \times 10^8$-$1 \times 10^{10}$ cells/individual, more preferably, $1 \times 10^9$-$1 \times 10^{10}$ cells/individual. While the differentiation of progenitor cells of pancreatic hormone-producing cells into pancreatic hormone-producing cells can utilize intracorporeal environment of the patient, it is also possible to administer a differentiation-inducing factor and the like used in the present invention from outside the body in an attempt to enhance differentiation efficiency and specificity. For the medicament of the present invention, pancreatic hormone-producing cells prepared using patient's own cells or cells of a donor showing cytocompatibility or histocompatibility type tolerable for the patient is preferably used. When sufficient cells cannot be achieved due to the age, constitution and the like, transplantation is also possible by embedding the cells in a capsule such as polyethylene glycol and silicon, a porous container and the like to avoid rejection. In this case, intraperitoneal or subcutaneous transplantation is also possible. The dose (amount to be transplanted) of the medicament of the present invention can be appropriately changed according to the age, body weight, symptom and the like of the patients who receive the administration.

3. Screening Method

The present invention provides a method of screening for a medicament (preferably therapeutic drug for diabetes), comprising using the cells obtained by any one or more steps selected from the group consisting of the following steps (1)-(4):

(1) a step of cultivating stem cells in a medium containing an activator of activin receptor-like kinase-4,7 and a GSK3 inhibitor
(2) a step of cultivating the cells obtained in the aforementioned step (1) in a medium containing an activator of activin receptor-like kinase-4,7
(3) a step of cultivating the cells obtained in the aforementioned step (2) in a medium containing any one or more kinds selected from the group consisting of (a) retinoic acid receptor agonists, (b) at least one kind selected from the group consisting of inhibitors of AMP-activated protein kinase and/or activin receptor-like kinase-2,3,6, and BMP antagonists, and (c) inhibitors of activin receptor-like kinase-4,5,7
(4) a step of cultivating the cells obtained in the aforementioned step (3);

(sometimes to be referred to as the "screening method of the present invention" in the present specification).

In another embodiment of the present invention, step (4) is performed in a medium containing at least one kind selected from the group consisting of (i) at least one kind selected from the group consisting of adenylate cyclase activators, cAMP phosphodiesterase inhibitors and cAMP analogs, (ii) steroids and (iii) ALK-4,5,7 inhibitors (further containing nicotinamide when desired).

The kind and concentration of various factors in the medium and the like are the same as those in the aforementioned production method of cells (1.).

The above-mentioned steps (1)-(4) can be performed in the same manner as in steps (1)-(4) of the production method of the above-mentioned pancreatic hormone-producing cells of the present invention.

Examples of the cells to be used for this screening include pancreatic hormone-producing cells obtained via the above-mentioned steps (1)-(4), progenitor cells of pancreatic hormone-producing cells obtained via the above-mentioned steps (1)-(3), endodermal cells obtained via the above-mentioned steps (1)-(2), and cells obtained via the above-mentioned step (1).

The screening method of the present invention is specifically performed as follows (embodiment 1).

(a) A method wherein pancreatic hormone-producing cells are cultured in the presence of a test compound and (b) a pancreatic hormone-producing cells are cultured in the absence of a test compound, an intracellular pancreatic hormone expression level and an extracellular pancreatic hormone secretion level are each measured, and compared.

As the expression level of pancreatic hormone, an expression level of a pancreatic hormone protein, an expression level of polynucleotide (e.g., mRNA and the like) encoding a pancreatic hormone protein and the like can be mentioned. The expression level and secretion level of a pancreatic hormone protein can be measured by a known method, for example, the aforementioned pancreatic hormone protein present in a cell extract, a medium and the like can be measured using an antibody recognizing a pancreatic hormone protein and according to a method such as Western blotting analysis, ELISA method and the like or a method analogous thereto and the like.

The mRNA level can be measured by a known method, for example, Northern hybridization, S1 mapping method, PCR method, quantitative RT-PCR method, DNA chip or array method or a method analogous thereto.

Cell culture is not particularly limited as long as it is performed under conditions where a pancreatic hormone can be expressed and/or secreted and can be performed according to a known method. Examples of a usable medium include MEM medium containing about 1-20% fetal bovine serum [Science, vol. 122, 501 (1952) etc.], DMEM medium [Virology, vol. 8, 396 (1959)], RPMI 1640 medium [The Journal of the American Medical Association vol. 199, 519 (1967)], and 199 medium [Proceeding of the Society for the Biological Medicine, vol. 73, 1 (1950)]. The pH of the medium is preferably about 6-8. Culture is performed at generally about 30° C.-40° C. for about 15 hr-5 days with aeration and stirring as necessary.

Examples of the test compound include peptide, protein, antibody, nonpeptidic compound, synthesis compound, fermentation product, cell extract, plant extract, animal tissue extract, plasma. Here, the test compound may form a salt. As the salt, a salt with physiologically acceptable acid (e.g., inorganic acid, organic acid), base (e.g., alkali metal salt, alkaline earth metal salt, aluminum salt) and the like is used. Examples of such salt include salts with inorganic acid (e.g., hydrochloric acid, phosphoric acid, hydrobromic acid, sulfuric acid), or salts with organic acid (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid), sodium salt, potassium salt, calcium salt, magnesium salt, barium salt and aluminum salt.

For example, a test compound that suppresses (inhibits) the expression level or secretion level of a pancreatic hormone in the above-mentioned (a) by not less than about 20%, preferably not less than 30%, more preferably not less than about 50%, as compared to those of the above-mentioned (b), can be selected as a compound that suppresses (inhibits) expression of pancreatic hormone in pancreatic hormone-producing cells.

A test compound that enhances the expression level or secretion level of a pancreatic hormone in the above-mentioned (a) by not less than about 20%, preferably not less than 30%, more preferably not less than about 50%, as compared to those of the above-mentioned (b), can be selected as a compound that enhances expression of pancreatic hormone in pancreatic hormone-producing cells.

When the pancreatic hormone-producing cells are insulin-producing cells, a compound that enhances insulin expression is useful as a therapeutic drug for diabetes. When the pancreatic hormone-producing cells are glucagon-producing cells, a compound that suppresses (inhibits) glucagon expression is useful as a therapeutic drug for diabetes.

Another embodiment of the screening method of the present invention is a method wherein (a) pancreatic hormone-producing cells are cultured in the presence of a test compound and (b) pancreatic hormone-producing cells are cultured in the absence of a test compound, a proliferative capacity of the cells is measured, and compared (embodiment 2). As the test compound to be used, those similar to the test compounds used in the above-mentioned embodiment 1 can be mentioned. The cell culture in this embodiment can be performed in the same manner as in the above-mentioned embodiment 1. As a method for measuring the proliferative capacity of a cell, a method generally used in this field can be used and includes, for example, a method of counting cell number, a method of evaluating uptake of $^3$H, 5-bromo-2'-deoxy-uridine (BrdU) and the like, ATP level, conversion level of tetrazolium compound to formazan product and the like.

For example, when the pancreatic hormone-producing cells are insulin-producing cells, a compound that significantly enhances growth of insulin-producing cells is useful as a therapeutic drug for diabetes. When the pancreatic hormone-producing cells are glucagon-producing cells, a compound that significantly suppresses (inhibits) growth of glucagon-producing cells is useful as a therapeutic drug for diabetes.

Another embodiment of the screening method of the present invention is a method wherein (a) progenitor cells of pancreatic hormone-producing cells are cultured in the presence of a test compound and (b) progenitor cells of pancreatic hormone-producing cells are cultured in the absence of a test compound, the level of differentiation of the cells is measured, and compared (embodiment 3). As the test compound to be used, those similar to the test compounds used in the above-mentioned embodiment 1 can be mentioned. The cell culture in this embodiment can be performed in the same manner as in the above-mentioned embodiment 1. The level of differentiation of progenitor cells of pancreatic hormone-producing cells can be examined by, for example, the presence or absence of expression of a marker specific to progenitor cells of pancreatic hormone-producing cells and/or pancreatic hormone-producing cells. Examples of the marker specific to progenitor cells of pancreatic hormone-producing cells include NGN3 (neurogenin 3), PAX4 (paired box 4), and examples of the marker specific to pancreatic hormone-producing cells include insulin, glucagon, pancreatic polypeptide, somatostatin, ghrelin, PCSK1 (proprotein convertase subtilisin/kexin type 1), SUR1 (sulfonylurea receptor 1, aka ATP-binding cassette, sub-family C(CFTR/MRP), member 8), glucokinase, MAFA (v-maf musculoaponeurotic fibrosarcoma oncogene homolog A), IAPP (islet amyloid polypeptide) and the like. In addition, the level of differentiation of progenitor cells of pancreatic hormone-producing cells can also be examined by the hormone secretion level when a substance that enhances hormone secretion is added. For example, when the pancreatic hormone-producing cells are insulin-producing cells, the level of differentiation of the insulin-producing cells can be evaluated by examining the insulin secretion level when a high concentration of glucose is added, by Western blotting method and ELISA (enzyme-linked immunosorbent assay) method.

For example, when the progenitor cells of pancreatic hormone-producing cells are progenitor cells of insulin-producing cells, a compound that significantly enhances differentiation of progenitor cells of insulin-producing cells is useful as a therapeutic drug for diabetes. When the progenitor cells of pancreatic hormone-producing cells are progenitor cells of glucagon-producing cells, a compound that significantly suppresses (inhibits) differentiation of progenitor cells of glucagon-producing cells is useful as a therapeutic drug for diabetes.

Another embodiment of the screening method of the present invention is a method wherein (a) endodermal cells are cultured in the presence of a test compound and (b) endodermal cells are cultured in the absence of a test compound, a proliferative or differentiation capacity of the cells is measured, and compared (embodiment 4). As the test compound to be used, those similar to the test compounds used in the above-mentioned embodiment 1 can be mentioned. The cell culture in this embodiment can be performed in the same manner as in the above-mentioned embodiment 1. As a method for measuring the proliferative capacity of endodermal cells, a method generally used in this field can be used and includes, for example, a method of counting cell number, a method of evaluating uptake of $^3$H, 5-bromo-2'-deoxy-uridine (BrdU) and the like, ATP level, conversion level of tetrazolium compound to formazan product and the like. The differentiation capacity of endodermal cells can be examined by, for example, the presence or absence of expression of a marker specific to endoderm cells. Examples of the marker specific to endoderm cells include α-fetoprotein, albumin, pepsin, pulmonary surfactant protein and the like. In general, differentiation induction and culture of endoderm cells are technically difficult as compared to those of mesoderm or ectoderm cells, and cells and/or endoderm differentiation-induction system prepared by utilizing a compound obtained by the screening method can be used for a new screening system for medicaments.

For example, when the endoderm cells are alveolar cells, a compound that enhances differentiation and growth of alveolar cells are useful as a therapeutic drug for emphysema and the like.

A medicament etc. that protect (maintain) function of pancreatic hormone-producing cells can be obtained by a method according to the screening method of the present invention. Another embodiment of the screening method of the present invention is a method wherein (a) pancreatic hormone-producing cells are cultured in the presence of a test compound and (b) pancreatic hormone-producing cells are cultured in the absence of a test compound, the number or function of viable cells are respectively measured, and compared (embodiment 5). As the test compound to be used, those similar to the test compounds used in the above-mentioned embodiment 1 can be mentioned. The cell culture in this embodiment can be performed in the same manner as in the above-mentioned embodiment 1. As a method for counting the viable cells, a method generally used in this field can be used and includes, for example, a method of counting cell number, a method of evaluating uptake of $^3$H, 5-bromo-2'-deoxy-uridine (BrdU) and the like, ATP level, conversion level of tetrazolium compound to formazan product and the like. In addition, the number of cells after induction of apoptosis can be quantified by, in addition to counting of the cells showing morphological characteristics (chromatin aggregation, nucleus fragmentation, cell contraction and the like), detection of fragmented DNA by TUNNEL (TdT-mediated dUTP nick end labeling) method and detection of the presence or absence of active caspase, and measurement of nuclear staining with live-cell impermeant dye 7-AAD (7-amino-actinomycin D) and the like, exposure of phosphatidylserine on cell surface, depolarization of mitochondria membrane, cleavage and degradation of particular intracellular protein and the like. As a method of determining the cell function, a method of measuring secretion level of insulin or C-peptide and variation in cellular membrane potential, which correspond to the glucose concentration, and the like can be mentioned. In this embodiment, a factor known to cause disorder in pancreatic hormone-producing cells, for example, inflammatory cytokine, active oxygen and production inducing substance thereof, high concentration of fatty acid, glucose and the like, is added during cell culture, and the number or function of viable cells is measured, and compared.

When pancreatic hormone-producing cells are insulin-producing cells, a compound that significantly enhances survival or functional maintenance of the insulin-producing cells against a factor known to cause disorder of the pancreatic hormone-producing cells is useful as a therapeutic drug for diabetes.

In addition, using the principle of the screening method of the present invention, cells in an undifferentiated state or progenitor cells in a differentiation-induction process can be obtained.

It is known that an antigen similar to a tumor antigen called "differentiation-associated antigen" such as carcinoembryonic antigen expresses in cells in an undifferentiated state or progenitor cells and the like in a differentiation-induction process. By searching expression of a novel antigen by a combination of a method such as proteome, glycome and the like and a method of bioinformatics, an anticancer agent can be screened for by using suppression of antigen expression itself, suppression of the growth of cancer cells that expresses the antigen, cell death and the like as indices. Alternatively, by administering these cells as they are or after denaturation treatment with formalin and the like, or a cellular membrane component after fractionation and purification, as immunogen, to an animal such as mouse, rat, rabbit, guinea pig, goat, chicken and the like, an antibody that cross-reacts with tumor cells is obtained, and an anticancer agent can be screened for by using reactivity with the antibody (increase/decrease of antigen level) as an index. Also, the obtained antibody itself can be used as a medicament or a diagnosis, or a purified antigen or a part thereof can be used as an antitumor vaccine.

Therefore, the present invention can provide a tool that enables detection of a novel "differentiation-associated antigen", and screening for an antibody against the antigen, a medicament or diagnosis containing the antibody, and the like.

Furthermore, using the principle of the screening method of the present invention, a compound that enhances differentiation of particular hormone-producing cells into different hormone-producing cells can be screened for. For example, after differentiation into glucagon-producing cells is induced, a compound that enhances transdifferentiation of glucagon-producing cells into insulin-producing cells can be screened for.

The level of transdifferentiation into particular pancreatic hormone-producing cells can be examined by measuring the expression level of a specific marker of pancreatic hormone-producing cells by quantitative RT-PCR method and the like, or the pancreatic hormone level secreted from pancreatic hormone-producing cells by Western blotting method, ELISA method and the like.

A medicament obtained by the above-mentioned screening method can be formulated according to a known method and using a physiologically acceptable additive (e.g., carrier, flavor, excipient, preservative, stabilizer, binder).

Examples of the dosage form of the thus-obtained preparation include oral preparations such as tablet applied with sugar coating as necessary, capsule, elixir, microcapsule and the like; and parenteral agents such as injection and the like. The content of the active ingredient (compound selected by the screening method of the present invention) in these preparations is, for example, 0.1-90 wt %.

Examples of the aforementioned additives include binders such as gelatin, cornstarch, tragacanth, gum arabic and the like; excipients such as crystalline cellulose and the like; swelling agents such as cornstarch, gelatin, alginic acid and the like; lubricants such as magnesium stearate and the like; sweetening agents such as sucrose, lactose, saccharin and the like; flavors such as peppermint, *Gaultheria adenothrix* oil, cherry and the like; liquid carriers such as fats and oils, water for injection, vegetable oil (e.g., sesame oil, palm oil, soybean oil), buffering agent (e.g., phosphate buffer, sodium acetate buffer) and the like; solubilizing agents (e.g., ethanol, propylene glycol, polyethylene glycol); non-ionic surfactant (e.g., polysorbate 80™, HCO-50); solubilizing agents (e.g., benzyl benzoate, benzyl alcohol); soothing agents (e.g., benzalkonium chloride, procaine hydrochloride); stabilizers (e.g., human serum albumin, polyethylene glycol); preservatives (e.g., benzyl alcohol, phenol); and antioxidants.

Examples of the aforementioned water for injection include saline; and an isotonic solution containing glucose, D-sorbitol, D-mannitol, sodium chloride or the like.

Since a medicament (preferably therapeutic drug for diabetes) obtained by the screening method of the present invention is safe and low toxic, it can be administered orally or parenterally to, for example, a mammal (e.g., human, mouse, rat, rabbit, sheep, swine, bovine, horse, cat, dog, monkey, chimpanzee).

The dose of the medicament is appropriately determined according to its action, the target disease, subject of administration, administration route and the like.

EXAMPLES

The present invention is explained in detail in the following by referring to Examples, which are not to be construed as limitative.

Example 1

Induction of Differentiation of Human iPS Cells into Endodermal Cells by Using Activin A and CHIR99021 [Step (1)-Step (2)]

As a first stage for induction of differentiation of human iPS cells (iPS cells obtained by introducing Oct3/4 gene, Klf4 gene and Sox2 gene: see Nat Biotechnol 2008; 26: 101-106) into pancreas cells (particularly pancreatic hormone-producing cells), differentiation of human iPS cells was induced into endodermal cells by using a 96 well plate.

As the human iPS cells, 253G1 strain (iPS cell line produced by expressing OCT4/SOX2/KLF4 with retrovirus; Nature Biotechnology 26, 101-106) was used. Maintenance culture of the iPS cells in an undifferentiated state was performed using mitomycin-treated mouse fibroblast (MEFs) seeded on a gelatin-coated plate as feeder cells, and a medium for primate ES cells (ReproCELL Incorporated) added with 4 ng/ml bFGF (PeproTech EC) and 0.5× Penicillin-streptomycin (SIGMA) as a medium at 37° C. under 5% $CO_2$. The medium was changed every day, the cell mass was detached every 4-5 days using a cell detachment solution for primate ES cell (ReproCELL Incorporated), and passaged by seeding on new feeder cells.

As a preculture for differentiation induction into endodermal cells, undifferentiated iPS cells were seeded in a 96 well plate. First, iPS cells maintained in a cell mass was treated with 0.25% trypsin-1 mM EDTA solution (GIBCO) and dissociated until they became single cells. Then, iPS cells dispersed in a medium were seeded in a 96 well plate at a density of $2\times10^4$ cells per well and cultured at 37° C. under 5% $CO_2$ for 1 day. The 96 well plate used had been gelatin-coated, seeded with $5\times10^3$ MEFs and cultured at 37° C. under 5% $CO_2$ for 5 hr. In addition, as a culture medium for seeding, a medium for primate ES cells added with 10 μM Y-27632 (Wako Pure Chemical Industries, Ltd.) was used. One day after seeding, the medium was changed to a medium for primate ES cells without Y-27632, and the cells were further cultured for 2 days until they became confluent.

Differentiation of iPS cells into endodermal cells was induced according to the following method. First, the confluent cells were washed with RPMI medium (GIBCO), RPMI medium containing various differentiation-inducing factors and 2% fetal bovine serum (FBS) was added, and the mixture was cultured for 1 day. As the differentiation-inducing factor, a combination of activin A (100 ng/ml) and CHIR99021 (3 µM), which is a GSK3β inhibitor, was used. After culture for one day, the cells were washed with RPMI medium, and further cultured for 2 days in RPMI medium added with 2% FBS and 100 ng/ml activin A. As a control, a part of the cells was cultured in RPMI medium added with 2% FBS alone for all 3 days.

As Comparative Example, iPS cells were treated in the same manner as in Example 1 except that only activin A (100 ng/ml) (Comparative Example 1), or a combination of activin A (100 ng/ml) and Wnt3a (25 ng/ml) (Comparative Example 2), was used as a differentiation-inducing factor.

To examine variation in the expression of endoderm differentiation marker when cultured under each condition, differentiation-induced cells were recovered over time, and the total RNA fractions were purified using RNeasy96 (Qiagen). Using a PrimeScript RT reagent kit (Takara Bio Inc.), cDNA was synthesized, and quantitative RT-PCR was performed, whereby the gene expression level of BRACHYURY, which is a primitive streak marker, and SOX17, which is an endodermal marker, was measured. The expression analysis results are shown in FIG. 1. By the addition of activin A and CHIR99021 for 1 day (Example 1), the expression level of BRACHYURY transiently increased one day after the differentiation induction. Thereafter, when these cells were further cultivated in a medium containing activin A alone for 2 days, the expression level of SOX17 increased markedly. On the other hand, when treated with Wnt3a generally used for endoderm induction along with activin A for 1 day (Comparative Example 2), the expression level of BRACHYURY was lower than with a treatment with CHIR99021. In addition, the expression level of SOX17 at 2 days later was also lower than with a treatment with CHIR99021.

Figure 2:
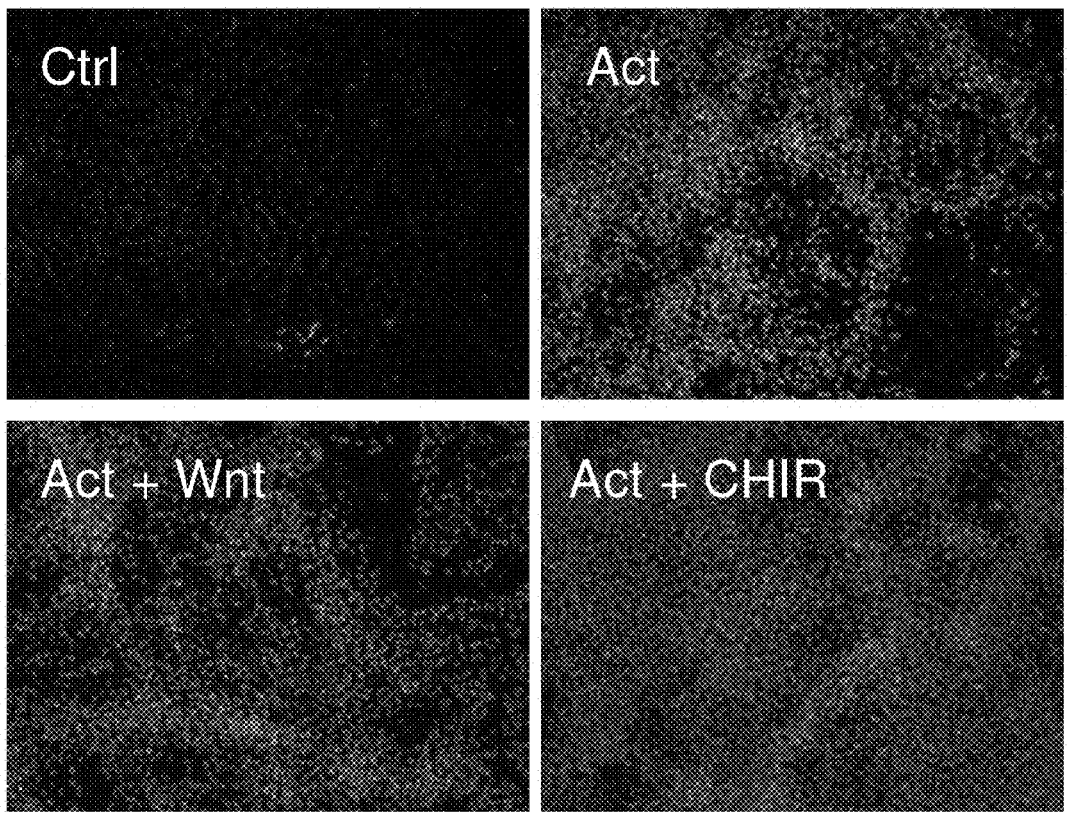
FIG. 2 shows the results of immunofluorescent staining, using an anti-human SOX17 antibody, of human iPS cells subjected to differentiation induction in the same manner as in FIG. 1 for 3 days. The nuclei of SOX17-positive cells are colored green with Alexa 488, and the nuclei of negative cells are colored blue with Hoechst 33342. When activin A and Wnt3a (Comparative Example 2) or CHIR99021 (Example 1) were combined, SOX17-positive cells were remarkably detected, and particularly when CHIR99021 was used (Example 1), the ratio of SOX17-positive cells were the highest.

To examine expression of SOX17 protein after culture for 3 days, immunofluorescent staining using an anti-SOX17 antibody was performed. After culture up to day 3 in the same manner as in FIG. 1, the cells were fixed with 2% paraformaldehyde (PFA) for 10 min and further for 20 min with 4% PFA at room temperature. The cells were reacted with anti-human SOX17 antibody (AF1924, R&D Systems) as the first antibody, sequentially reacted with Alexa 488-labeled second antibody (Invitrogen) as the second antibody, and observed with a fluorescence microscope. The results are shown in FIG. 2. When activin A and CHIR99021 were added as a differentiation-inducing factor (Example 1), most of the cells were observed to have expressed SOX17 protein. When only activin A was added (Comparative Example 1) and when activin A and Wnt3a were added (Comparative Example 2), a part of the cells also expressed SOX17 protein; however, the ratio thereof was lower as compared to the addition of activin A and CHIR99021.

From the above-mentioned investigation, it has been clarified that culture in a medium added with activin A and CHIR99021 for 1 day, and further for 2 days in a medium added with activin A alone can efficiently induce differentiation into endodermal cells.

Examples 2-8

Induction of Differentiation of Endodermal Cell into Progenitor Cells of Pancreatic Hormone-Producing Cells by Using Retinoic Acid, Dorsomorphin and SB431542 [Step (3)]

The cells differentiated into endodermal cells were further induced to differentiate into progenitor cells of pancreatic hormone-producing cells.

The cells induced to differentiate into endodermal cells according to the method shown in Example 1 was washed with Improved MEM Zinc Option medium (Invitrogen), and the medium was changed to Improved MEM Zinc Option medium (Invitrogen) containing 1% B-27 (GIBCO) and added with a combination of dorsomorphin (1 µM), retinoic acid (2 µM) and SB431542 (10 µM) (Example 2). The dorsomorphin is an inhibitor of AMP-activated protein kinase (AMPK), and an inhibitor of ALK2, ALK3 and ALK6 from among activin receptor-like kinases (ALK). In addition, SB431542 is an inhibitor of ALK4, ALK5 and ALK7 from among ALKs. After medium exchange, the cells were cultured under the conditions of 37° C., 5% $CO_2$ for 6 days, and the expression levels of pancreatic progenitor cells marker PDX1 and progenitor cells of pancreatic hormone-producing cells marker NGN3 were measured in the same manner as in Example 1.

The endodermal cells were treated in the same manner as in Example 2 except that retinoic acid alone (Example 3), SB431542 alone (Example 4), a combination of retinoic acid and SB431542 (Example 5), dorsomorphin alone (Example 6), a combination of dorsomorphin and retinoic acid (Example 7) and a combination of dorsomorphin and SB431542 (Example 8) were used.

Figure 3:
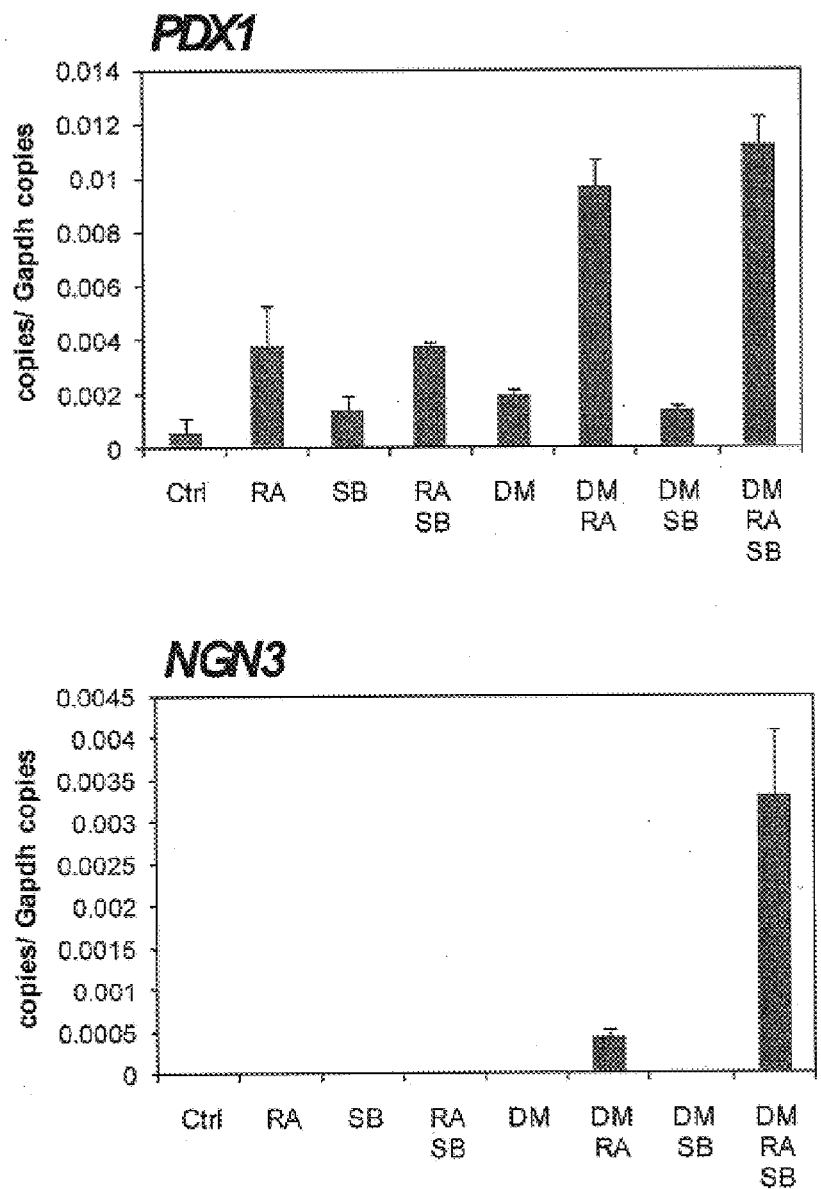
FIG. 3 shows the results obtained by obtaining cells by induction of differentiation from human iPS cells for 3 days by using activin A (addition for 3 days) and CHIR99021 (added simultaneously with activin A only the first day), further culturing the cells with the addition of various differentiation-inducing factors from day 3 to day 9, and measuring the expression of pancreatic progenitor cells marker (PDX1) and progenitor cells of pancreatic hormone-producing cells marker (NGN3) on day 9 by quantitative RT-PCR. The results are shown as relative values to the expression level of a housekeeping gene GAPDH. As a differentiation-inducing factor, retinoic acid (RA), SB431542 (SB) and dorsomorphin (DM), each alone or in combination shown in the Figure (Examples 2-8) were used, and a part of the cells were cultured as a control (Ctrl) without addition of a differentiation-inducing factor. PDX1 showed a remarkably high value when retinoic acid and dorsomorphin were added in combination (Example 2, Example 7), and NGN3 showed the highest value when 3 kinds of retinoic acid, SB431542 and dorsomorphin were combined (Example 2).

The expression analysis results are shown in FIG. 3. When dorsomorphin, retinoic acid and SB431542 were simultaneously added (Example 2) and the mixture was cultivated for 6 days, the expression levels of PDX1 and NGN3 increased markedly. When a combination of dorsomorphin and retinoic acid (Example 7) was added, the expression of PDX1 greatly increased; however, the expression of NGN3 did not show a significant increase. Expression of PDX1 and NGN3 did not vary remarkably under other conditions. From these results, it has been clarified that addition of dorsomorphin and retinoic acid induced differentiation into pancreatic progenitor cells that expresses PDX1, and further addition of SB431542 to dorsomorphin and retinoic acid also induced differentiation into progenitor cells of pancreatic hormone-producing cells that expresses NGN3, in addition to the differentiation into pancreatic progenitor cells.

Figure 4:
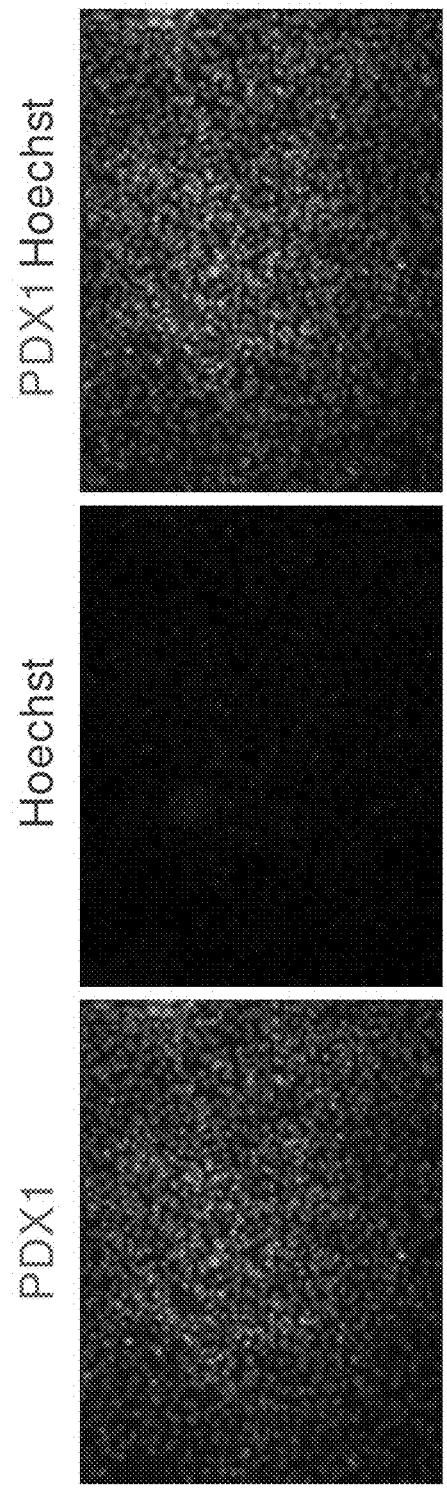
FIG. 4 shows the results of immunofluorescent staining, using an anti-human PDX1 antibody, of the cells after differentiation induction in the same manner as in FIG. 3 for 9 days under the conditions using 3 kinds of retinoic acid, SB431542 and dorsomorphin in combination (Example 2). The nuclei of PDX1-positive cells are colored green with Alexa 488, and the nuclei of negative cells are colored blue with Hoechst 33342. Most of the cells are PDX1-positive, and the method of the present invention induces differentiation into pancreatic progenitor cells with extremely high efficiency.

To examine expression of PDX1 protein after culture for 9 days, immunostaining with anti-PDX1 antibody was performed. Dorsomorphin, retinoic acid and SB431542 were added to the cell differentiated into an endodermal cell (Example 2) and they were cultured for 6 days. 4% PFA was added to fix the cells at room temperature for 30 min. Furthermore, the cells were reacted with anti-human PDX1 antibody (AF2419, R&D Systems) as the first antibody, and sequentially reacted with Alexa 488-labeled second antibody (Invitrogen) as the second antibody, and the cells were observed with a fluorescence microscope. The results are shown in FIG. 4. Most of the cells were observed to have expressed PDX1 protein. From the results, it was confirmed that differentiation toward the pancreas was induced in most of the cells.

Examples 9-15

Induction of Differentiation of Pancreatic Progenitor Cells into Pancreatic Hormone-Producing Cells [Step (4)]

A method of inducing further differentiation of the later process in cells induced to differentiate into progenitor cells of pancreatic hormone-producing cells was considered.

Figure 5:
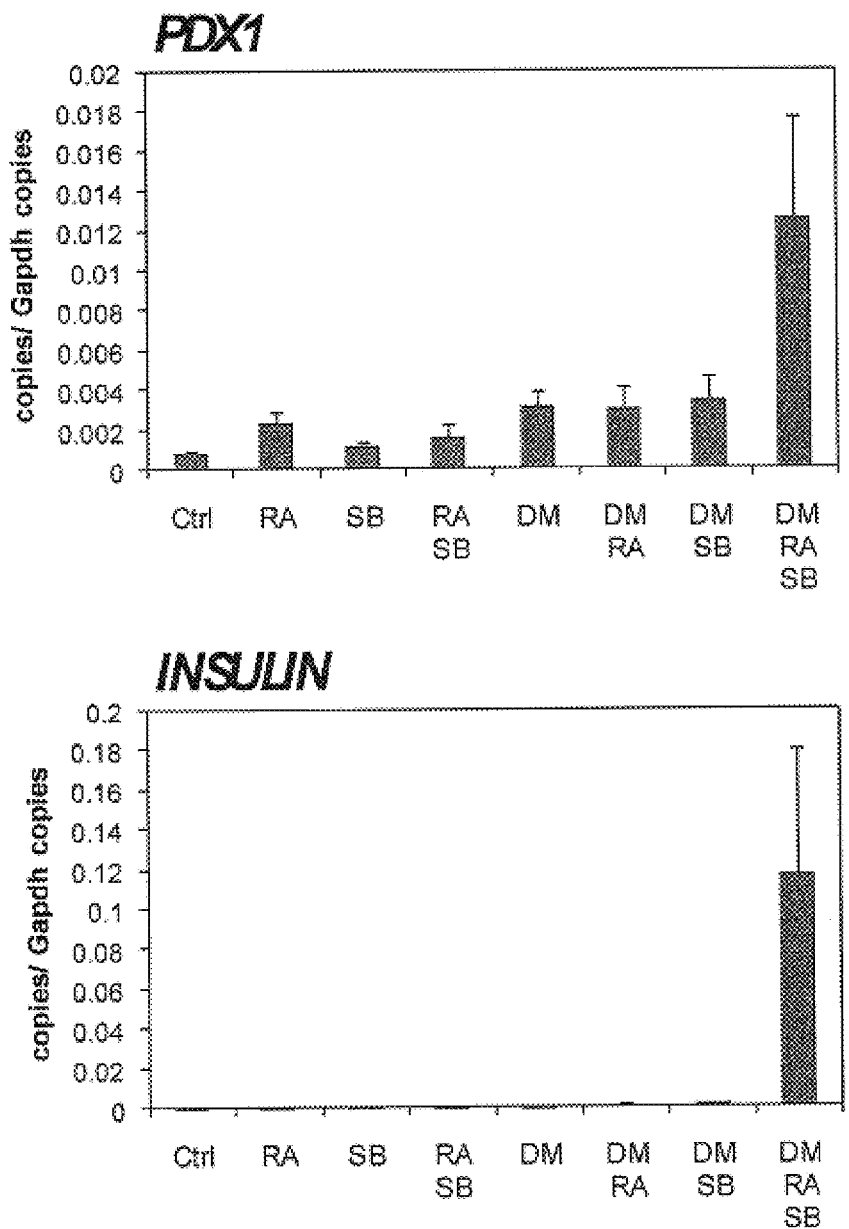
FIG. 5 shows the results obtained by obtaining cells by induction of differentiation from human iPS cells for 3 days by using activin A (addition for 3 days) and CHIR99021 (added simultaneously with activin A only the first day), inducing differentiation in the same manner as in the method of FIG. 3 by using differentiation-inducing factor alone or in combination for 6 days from day 3 to day 9, further culturing the cells in a medium free of a differentiation-inducing factor for 6 days from day 9 to day 15 (Examples 9-15), and measuring the expression levels of PDX1 and insulin by quantitative RT-PCR. The results are shown as relative values to the expression level of a housekeeping gene GAPDH. Both PDX1 and insulin showed the highest value when 3 kinds of retinoic acid, SB431542 and dorsomorphin were combined (Example 9).

To the cells differentiated into endoderm according to the method shown in Example 1 was added a differentiation-inducing factor (dorsomorphin, retinoic acid and SB431542 each singly or a combination thereof) in the same manner as in Examples 2-8. After culturing from day 3 to day 9, the cells were washed with Improved MEM Zinc Option medium (Invitrogen), and the medium was changed to Improved MEM Zinc Option medium (Invitrogen) added with 1% B-27 (GIBCO), and further cultured for 6 days (up to day 15 from the start of differentiation induction). In Example 9, a combination of dorsomorphin, retinoic acid and SB431542 was added; in Example 10, retinoic acid alone was added; in Example 11, SB431542 alone was added; in Example 12, a combination of retinoic acid and SB431542 was added; in Example 13, dorsomorphin alone was added; in Example 14, a combination of dorsomorphin and retinoic acid was added; and in Example 15, a combination of dorsomorphin and SB431542 was added. The expression level of PDX1, which is pancreatic progenitor cells marker, and insulin, which is pancreatic β cells (insulin-producing cells) marker, was measured in the same manner as in Example 1. The expression analysis results are shown in FIG. 5. Only in the cell made to highly express NGN3 by simultaneous addition of dorsomorphin, retinoic acid and SB431542 (Example 9) until day 9 of culture, expression of insulin was remarkably induced on day 15 of culture. In this case, the expression level of PDX1 was also high as compared to other conditions.

Figure 6:
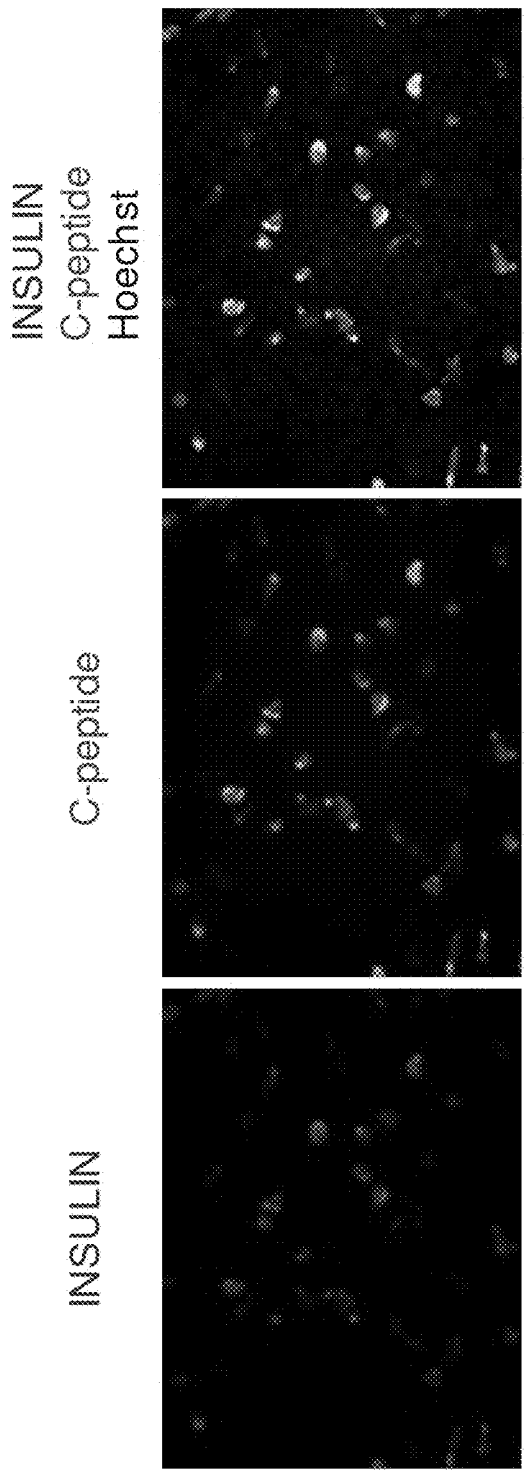
FIG. 6 shows the results of immunofluorescent staining, using an anti-insulin antibody and an anti-human C-peptide antibody, of the cells of Example 9 after 15 days of differentiation induction. The insulin-producing cells (insulin-positive cells) are colored red with Alexa 568, C-peptide-positive cells are colored green with Alexa 488, and the nuclei of the cells are colored blue with Hoechst 33342. When respective stained images are merged, they were colored yellow since the insulin-producing cells and the C-peptide-positive cells show a match.

To examine expression of insulin and C-peptide proteins, immunofluorescent staining using an anti-insulin antibody and an anti-C-peptide antibody was performed. Dorsomorphin, retinoic acid and SB431542 were added to the cell differentiated into endoderm and the mixture was cultured for 6 days. The medium was changed to Improved MEM Zinc Option medium (Invitrogen) containing 1% B-27 and the cells were further cultured for 6 days (Example 9). After the culture, the cells were fixed with 2% PFA at 4° C. overnight. Thereafter, the cells were reacted with an anti-insulin antibody (A0564, DAKO) or anti-human C-peptide antibody (C-PEP-01, MONOSAN) as the first antibody, and sequentially reacted with Alexa 488-labeled second antibody (Invitrogen) or Alexa 568-labeled second antibody (Invitrogen) as the second antibody, and observed with a fluorescence microscope. The results of the immunofluorescent staining are shown in FIG. 6. A number of cells expressing insulin and C-peptide were observed. In addition, when fluorescence images were merged, most of the stained cells were colored yellow, and it was confirmed that the same cells are stained with the anti-insulin antibody and anti-C-peptide antibody. Since a large amount of insulin is also contained in the medium, the cells may uptake insulin in the medium and become pseudo-positive. However, since they are also stained even with C-peptide antibody not added to the medium, expression of insulin protein in the cell was confirmed.

Experimental Example 1

Figure 7:
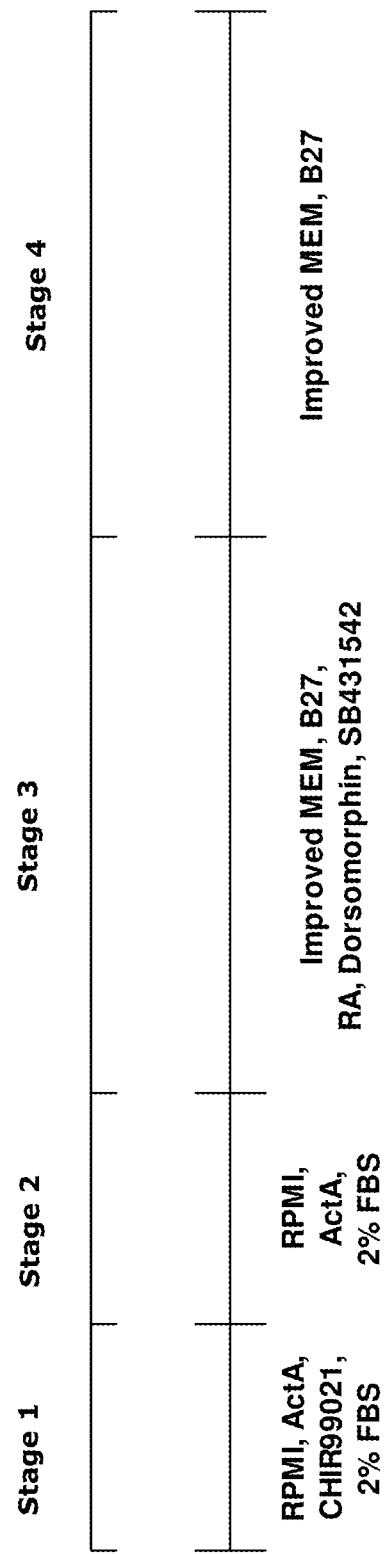
FIG. 7 shows the outline of a method of differentiation induction into pancreatic cells. The differentiation induction method consists of 4 stages, and can induce differentiation into pancreas lineage cells by adding a basal medium and a growth differentiation factor in combination in the order shown in the Figure to undifferentiated human iPS cells.

Variation in Expression of Each Differentiation Marker In Differentiation-Induction Process Based on the results of Examples 1-15, a pancreas differentiation induction system consisting of 4 stages shown in FIG. 7 was set, and variation in the expression of various differentiation markers in a differentiation-induction process of undifferentiated iPS cells towards pancreas was examined.

Figure 8:
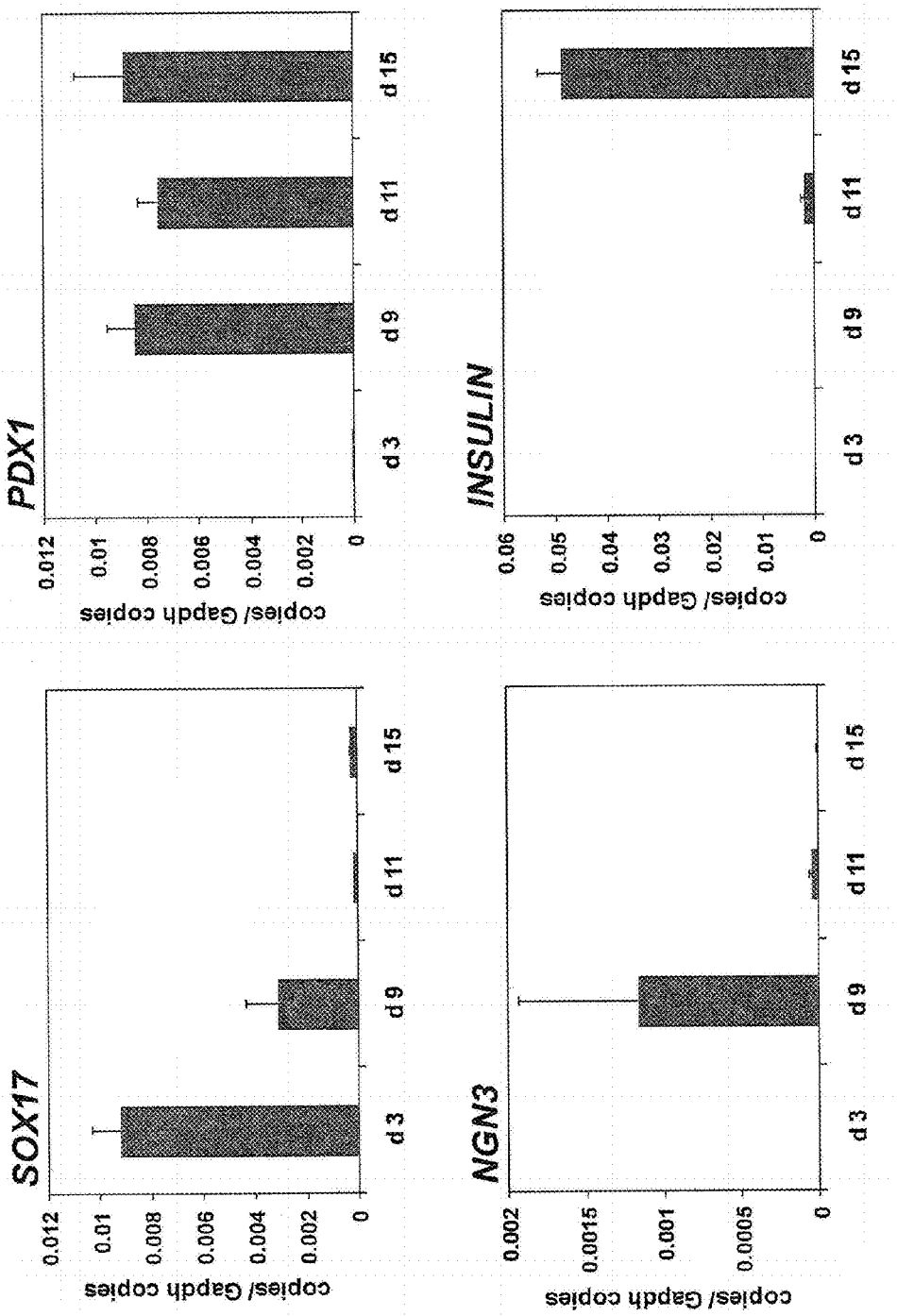
FIG. 8 shows the manner of expression of various differentiation markers when differentiation was induced according to the method shown in FIG. 7. The expression levels of various genes were measured at day 3, day 9, day 11 and day 15 of differentiation induction, and the results are shown as relative values to the expression level of a housekeeping gene GAPDH. The endodermal marker SOX17 showed a high value in the early stage of differentiation induction, and sustained expression of pancreatic progenitor cells marker PDX1 was observed by a differentiation induction treatment using 3 kinds of retinoic acid, SB431542 and dorsomorphin in combination. Moreover, progenitor cells of pancreatic hormone-producing cells marker NGN3 temporarily showed a high value in the early stage of period when PDX1 was expressed, and expression of pancreatic β cells marker insulin was detected in the latter stage of the differentiation induction treatment.

In stage 1, activin A (100 ng/ml) and CHIR99021 (3 µM) were added to RPMI medium containing 2% FBS, and the mixture was cultured for 1 day. In stage 2, activin A (100 ng/ml) was added to RPMI medium containing 2% FBS and the mixture was cultured for 2 days. In stage 3, 3 kinds of dorsomorphin (1 µM), retinoic acid (2 µM) and SB431542 (2 µM) were simultaneously added to Improved MEM Zinc Option medium (Invitrogen) containing 1% B-27, and the mixture was cultured for 6 days. In stage 4, the cells were further cultured for 6 days in Improved MEM Zinc Option medium (Invitrogen) containing 1% B-27. After culture, the time-course variations in the expression of various differentiation markers were measured in the same manner as in Example 1. The expression analysis results are shown in FIG. 8.

The expression of SOX17, which is an endodermal marker, was remarkably induced on day 3 of culture, and thereafter decreased gradually. The expression of PDX1 increased on day 9 of culture, and the expression level was maintained until day 15 of culture. The expression of NGN3 temporarily increased on day 9 of culture, and the expression level after day 11 of culture decreased drastically. The expression of insulin drastically increased from day 15 of culture. These results match well with the gene expression pattern until the pancreas is formed in the developmental process, and it has been clarified that use of the present differentiation-induction system can induce differentiation into pancreatic cells in the form of mimicking the pancreatic development.

Example 16

Induction of Differentiation of Progenitor Cells of Pancreatic Hormone-Producing Cells into Pancreas Cells [Step (4); Treatment with Forskolin and Nicotinamide]

In step (4), a factor that increases the differentiation efficiency into insulin-expressing cells was searched. As a result, the differentiation efficiency into insulin-expressing cells was found to increase by simultaneous addition of forskolin and nicotinamide in step (4).

Figure 9:
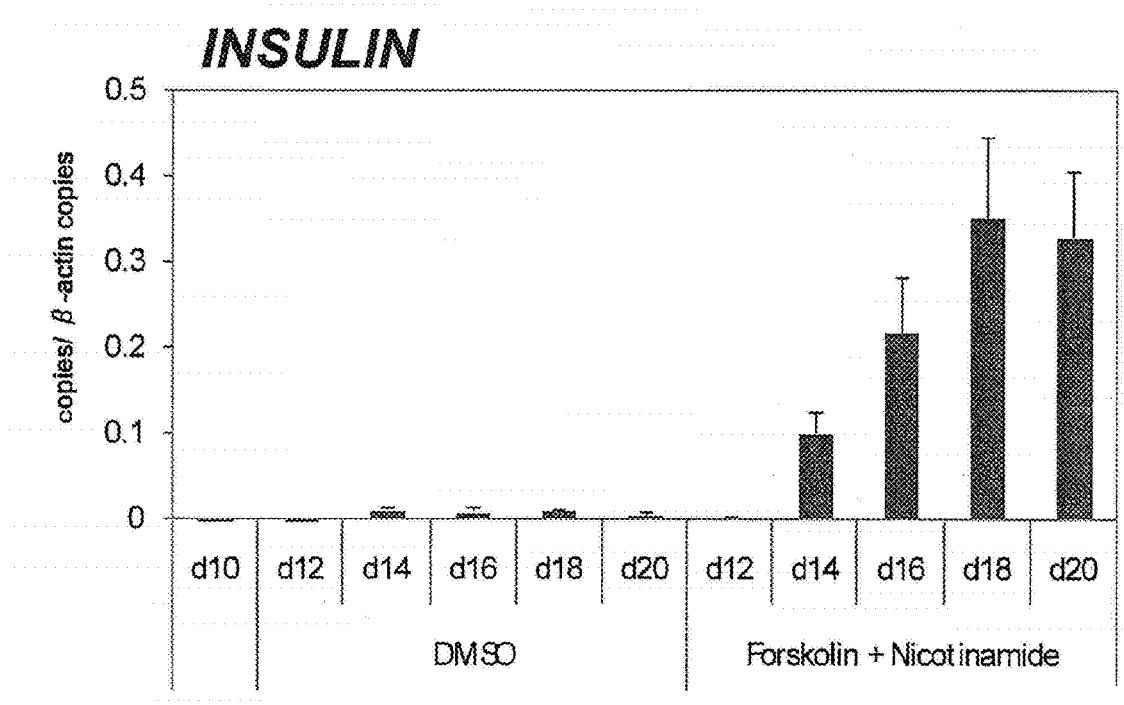
FIG. 9 shows the manner of expression of insulin when differentiation was induced by simultaneous addition of forskolin and nicotinamide or addition of DMSO alone in the differentiation induction method, step (4). The expression levels of insulin at day 10, day 12, day 14 day 16, day 18 and day 20 of differentiation induction are shown as relative values to the expression level of a housekeeping gene β-actin. By simultaneous addition of forskolin and nicotinamide, insulin expression was enhanced from day 14 and maintained up to day 20 of the induction.

Endodermal cells were induced according to the method shown in Example 1, 3 kinds of dorsomorphin (1 µM), retinoic acid (2 µM) and SB431542 (10 µM) were simultaneously added to Improved MEM Zinc Option medium (Invitrogen) containing 1% B-27, and the cells were cultured for 7 days. The medium was changed once on day 7 of induction. The cells on day 10 of induction were washed with Improved MEM Zinc Option medium, the medium was changed to Improved MEM Zinc Option medium containing 1% B-27 (GIBCO) and added with forskolin (10 µM) and nicotinamide (10 mM), or a medium added with 0.1% DMSO as a control, and the cells were further cultured for 10 days or 12 days (Example 16). The medium was changed every 3-4 days. After culture, the expression level of insulin was measured in the same manner as in Experimental Example 1. The expression analysis results are shown in FIG. 9. The cells cultured in the medium added with forskolin and nicotinamide showed high expression of insulin from day 14 of induction as compared to the cells added with DMSO, and the expression was maintained until day 20 of culture.

Figure 10:
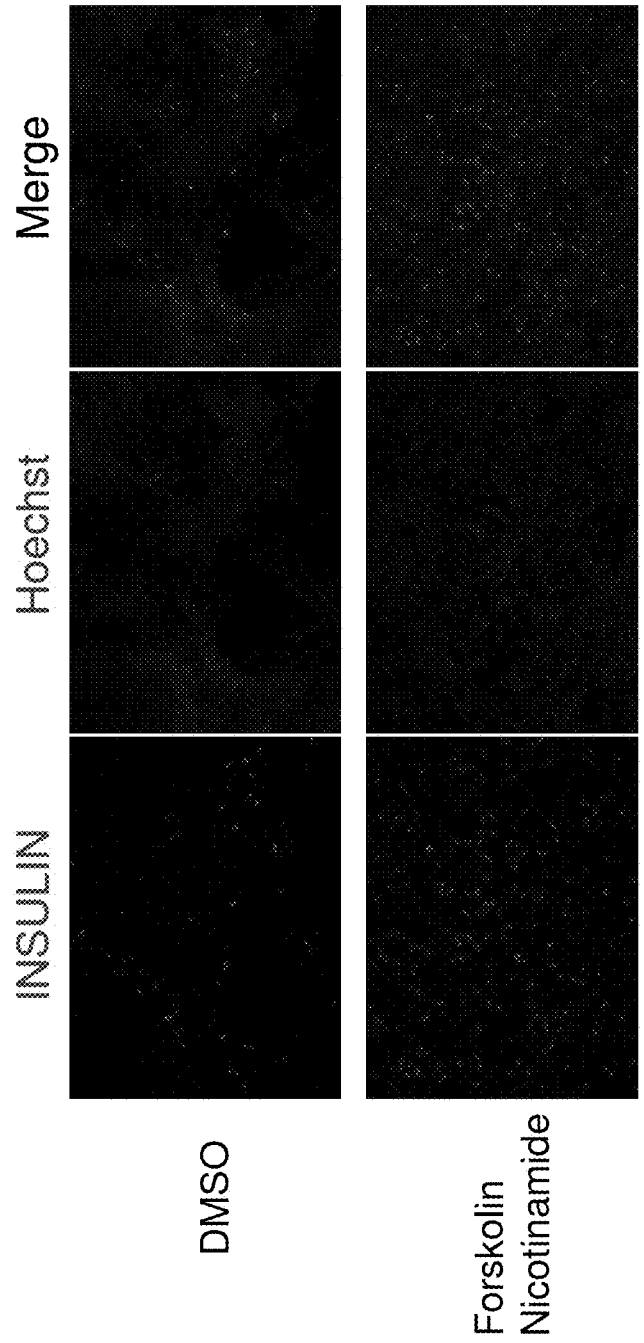
FIG. 10 shows the results of immunofluorescent staining, using an anti-insulin antibody, of the cells obtained by differentiation induction in the same manner as in the present differentiation induction method, step (4) (differentiation induction from day 10 to day 22) with simultaneously addition of forskolin and nicotinamide, or addition of DMSO alone. The insulin-producing cells (insulin-positive cells) are colored red with Alexa 568, and the nuclei of the cells are colored blue with Hoechst 33342. The simultaneous addition of forskolin and nicotinamide induces differentiation into insulin-producing cells highly efficiently.

To examine expression of insulin protein, immunofluorescent staining with an anti-insulin antibody was performed. The cells on day 22 of induction, whose differentiation was induced in the same manner as above, were fixed with 2% PFA at 4° C. overnight. Thereafter, the cells were sequentially reacted with an anti-insulin antibody (A0564, DAKO) as the first antibody and Alexa 568-labeled second antibody (Invitrogen) as the second antibody, and observed with a fluorescence microscope. The results of immunostaining are shown in FIG. 10. When cultured with the addition of forskolin and nicotinamide (Example 16), a high ratio of insulin-producing cells relative to the total cell number was observed as compared to that with the addition of DMSO.

From these results, it has been shown that simultaneous addition of forskolin and nicotinamide can induce differentiation into insulin-producing cells with high efficiency.

Examples 17-31

Induction of Differentiation of Progenitor Cells of Pancreatic Hormone-Producing Cells into Pancreas Cells [Step (4); Treatment with Forskolin, Nicotinamide, Dexamethasone, ALK5 Inhibitor II]

Besides forskolin and nicotinamide, in step (4), a factor that increases differentiation efficiency into insulin-expressing cells was searched. As a result, differentiation efficiency into an insulin-expressing cells was found to increase when dexamethasone or ALK5 inhibitor II (2-(3-(6-methylpyridin-2-yl)-1H-pyrazol-4-yl)-1,5-naphthyridine) was added in step (4).

Endodermal cells were induced according to the method shown in Example 1, 3 kinds of dorsomorphin (1 μM), retinoic acid (2 μM) and SB431542 (10 μM) were simultaneously added to Improved MEM Zinc Option medium (Invitrogen) containing 1% B-27, and the cells were cultured for 7 days. The medium was changed once on day 7 of induction. The cells on day 10 of induction were washed with Improved MEM Zinc Option medium, the medium was changed to Improved MEM Zinc Option medium containing 1% B-27 (GIBCO) and added with one or more kinds of inducing factors from forskolin (10 μM), nicotinamide (10 mM), dexamethasone (10 μM) and ALK5 inhibitor II (5 μM), or a medium without the aforementioned inducing factors as a control, and the cells were further cultured for 10 days. The medium was changed every 5 days.

Figure 11:
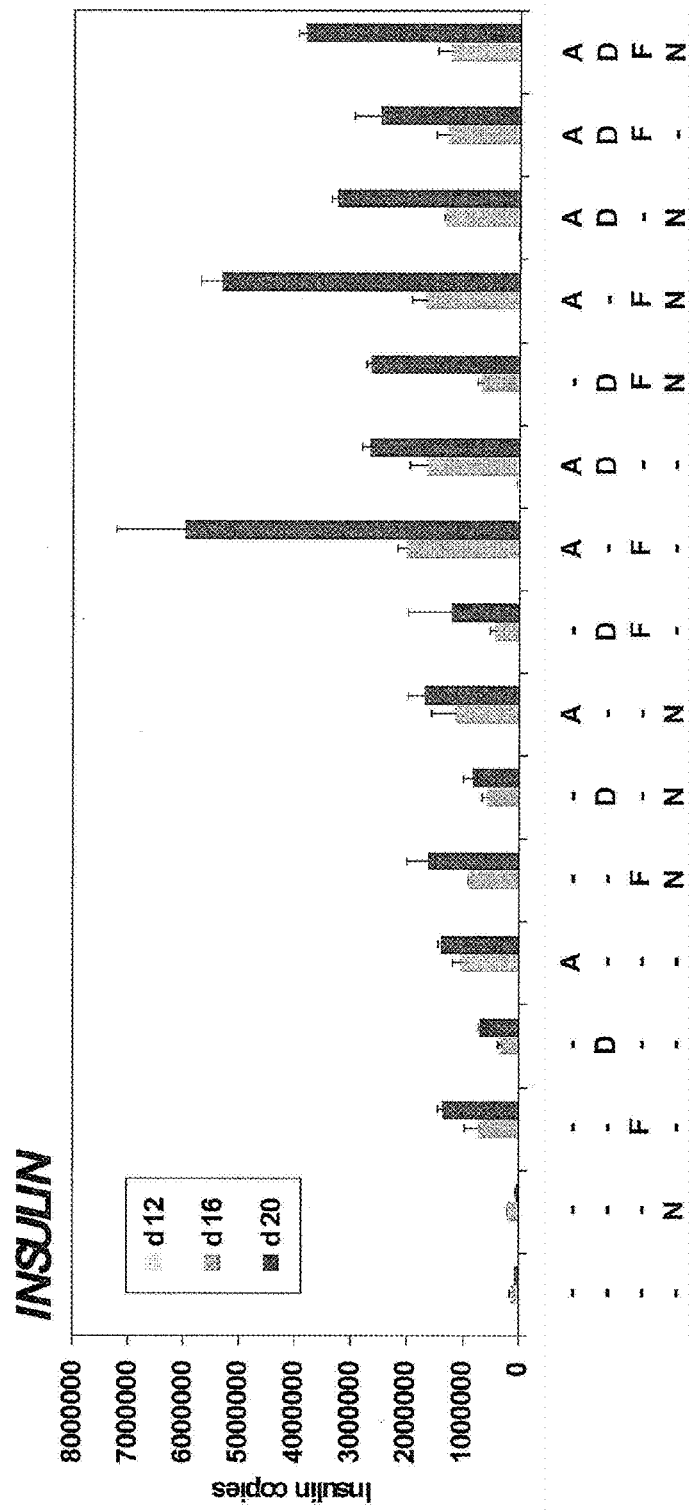
FIG. 11 shows the manner of expression of insulin when differentiation was induced by the addition of forskolin, nicotinamide, dexamethasone, ALK5 inhibitor II each alone or in combination in the present differentiation induction method, step (4). In the Figure, N shows nicotinamide, F shows forskolin, D shows dexamethasone, and A shows ALK5 inhibitor II. After addition of the factors in the combinations shown in the Figure and cultivation, the expression level of insulin at day 12, day 16 and day 20 of induction was measured. When forskolin, dexamethasone or ALK5 inhibitor II was added each alone, or in combination of forskolin, nicotinamide, dexamethasone and ALK5 inhibitor II in step (4), the insulin expression showed a high value.

In Example 17, nicotinamide alone was added; in Example 18, forskolin alone was added; in Example 19, dexamethasone alone was added; in Example 20, ALK5 inhibitor II alone was added; in Example 21, nicotinamide and forskolin were added; in Example 22, nicotinamide and dexamethasone were added; in Example 23, nicotinamide and ALK5 inhibitor II were added; in Example 24, forskolin and dexamethasone were added; in Example 25, forskolin and ALK5 inhibitor II were added; in Example 26, dexamethasone and ALK5 inhibitor II were added; in Example 27, nicotinamide, forskolin and dexamethasone were added; in Example 28, nicotinamide, forskolin and ALK5 inhibitor II were added; in Example 29, nicotinamide, dexamethasone and ALK5% inhibitor II were added; in Example 30, forskolin, dexamethasone and ALK5 inhibitor II were added; and in Example 31, nicotinamide, forskolin, dexamethasone and ALK5 inhibitor II were added. After culture under each condition, the expression levels of insulin in the cells on day 12 of differentiation induction, on day 16 of differentiation induction and day 20 of differentiation induction were measured in the same manner as in Example 1. The expression analysis results are shown in FIG. 11. Forskolin (Example 18), dexamethasone (Example 19) and ALK5 inhibitor II (Example 20) were each added singly, and the insulin expression increased markedly. Furthermore, when two or more kinds from forskolin, nicotinamide, dexamethasone and ALK5 inhibitor II were added in combination (Examples 21-31), the insulin expression level increased markedly.

Figure 12:
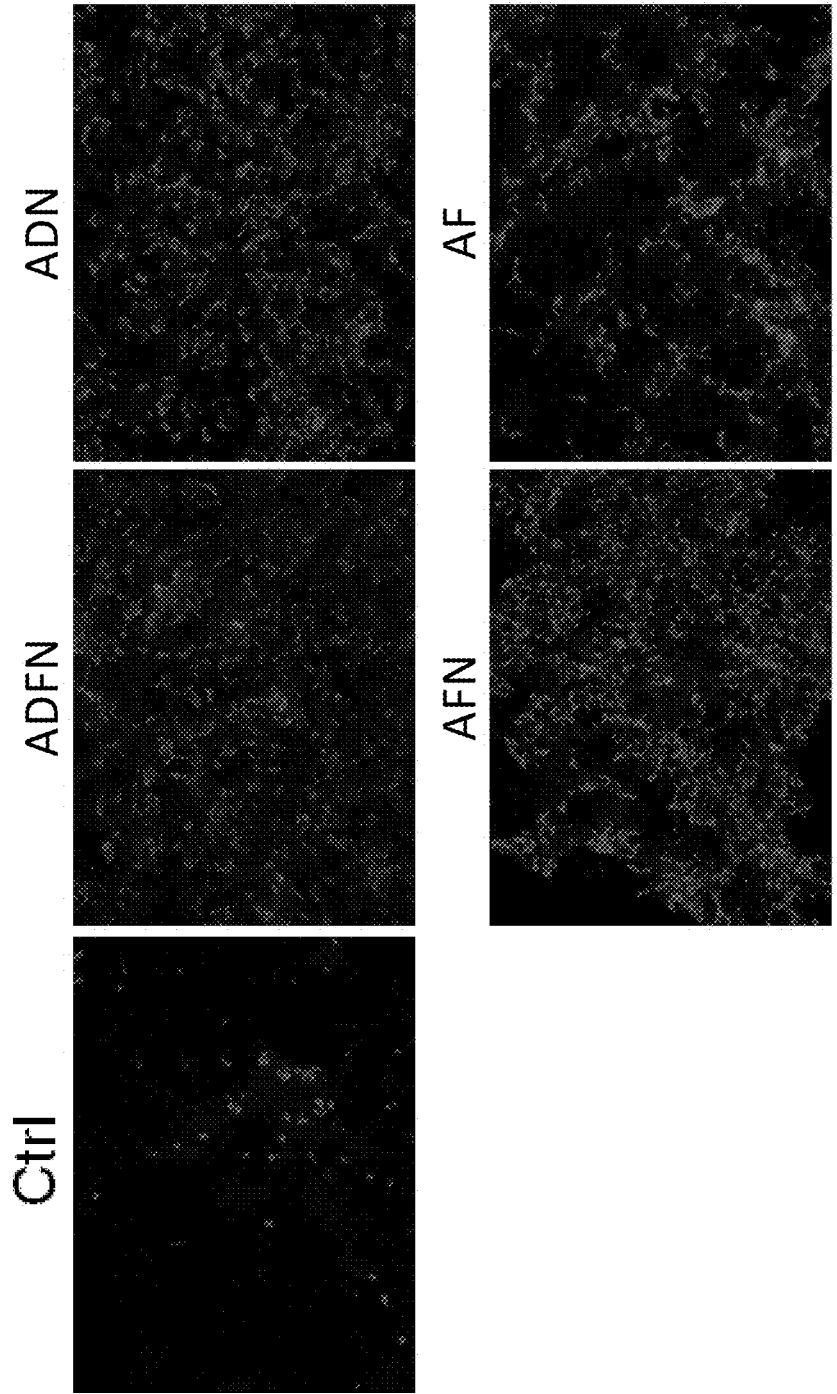
FIG. 12 shows the results of immunofluorescent staining, using an anti-insulin antibody, of the cells obtained by differentiation induction in the same manner as in the present differentiation induction method, step (4) (differentiation induction from day 10 to day 20) with the addition of forskolin, nicotinamide, dexamethasone and ALK5 inhibitor II in the combinations shown in the Figure or without addition of an inducing factor as a control. In the Figure, N shows nicotinamide, F shows forskolin, D shows dexamethasone, and A shows ALK5 inhibitor II. The insulin-producing cells (insulin-positive cells) are colored red with Alexa 568, and the nuclei of the cells are colored blue with Hoechst 33342. The addition of forskolin, nicotinamide, dexamethasone and ALK5 inhibitor II in combination induces differentiation into insulin-producing cells highly efficiently.

To examine expression of insulin at a protein level when forskolin, nicotinamide, dexamethasone and ALK5 inhibitor II are added in combination, immunofluorescent staining with an anti-insulin antibody was performed. Endodermal cells were induced according to the method shown in Example 1, 3 kinds of dorsomorphin (1 μM), retinoic acid (2 μM) and SB431542 (10 μM) were simultaneously added to Improved MEM Zinc Option medium (Invitrogen) containing 1% B-27, and the cells were cultured for 7 days. The medium was changed once on day 7 of induction. The cells on day 10 of induction were washed with Improved MEM Zinc Option medium, the medium was changed to, as a medium that induced insulin expression at a particularly high value in the above-mentioned experiment, Improved MEM Zinc Option medium containing 1% B-27 (GIBCO) and added with forskolin, nicotinamide, dexamethasone and ALK5 inhibitor II (Example 31), said medium added with forskolin, nicotinamide and ALK5 inhibitor II (Example 28), said medium added with nicotinamide, dexamethasone and ALK5 inhibitor II (Example 29), said medium added with forskolin and ALK5 inhibitor II (Example 25), or said medium without addition of an inducing factor as a control, and the cells were further cultured for 10 days. The medium was changed every 5 days. After culture, the cells were fixed with 2% PFA for 10 min and further with 4% PFA for 20 min at room temperature. Thereafter, the cells were sequentially reacted with an anti-insulin antibody (A0564, DAKO) as the first antibody, and with Alexa 568-labeled second antibody (Invitrogen) as the second antibody, and observed with a fluorescence microscope. The results of the immunofluorescent staining are shown in FIG. 12. It was observed that addition of forskolin, nicotinamide, dexamethasone and ALK5 inhibitor II in combination remarkably increased the ratio of insulin-producing cells. These results matches well with the aforementioned results that expression of insulin at an mRNA level under each culture condition increased markedly. From the above results, it has been clarified that addition of forskolin, dexamethasone and ALK5 inhibitor II each singly, or two or more kinds from forskolin, nicotinamide, dexamethasone and ALK5 inhibitor II in combination more efficiently induces differentiation of pancreatic progenitor cells into insulin-producing cells.

Examples 32-34

Induction of Differentiation of Human iPS Cells into Endodermal Cells by Using a Compound Other than CHIR99021 as GSK3 Inhibitor [Step (1)]

Whether even use of a GSK3 inhibitor other than CHIR99021 in step (1) enables differentiation induction into endodermal cells was examined. The differentiation of human iPS cells into endodermal cells was induced according to the following method. First, human iPS cells at confluence were prepared in the same manner as in Example 1. Thereafter, the cells were washed with RPMI medium (GIBCO), and cultured for 1 day in RPMI medium containing various GSK3 inhibitors, activin A (100 ng/ml) and 2% fetal bovine serum (FBS). As the GSK3 inhibitors, CHIR99021 (3 μM), SB415286 (3-[(3-chloro-4-hydroxyphenyl)amino]-4-(2-nitrophenyl)-1H-pyrrole-2,5-dione, 3 μM) and SB216763 (3-(2,3-dichlorophenyl)-4-(1-methyl-1H-indol-3-yl)-1H-pyrrole-2,5-dione, 20 μM) were used. As a control, the cells were treated with a medium added only with activin A and free of GSK3 inhibitor. After culture for 1 day, the cells were washed with RPMI medium, and further cultured for 2 days in RPMI medium added with 2% FBS and 100 ng/ml activin A.

Figure 13:
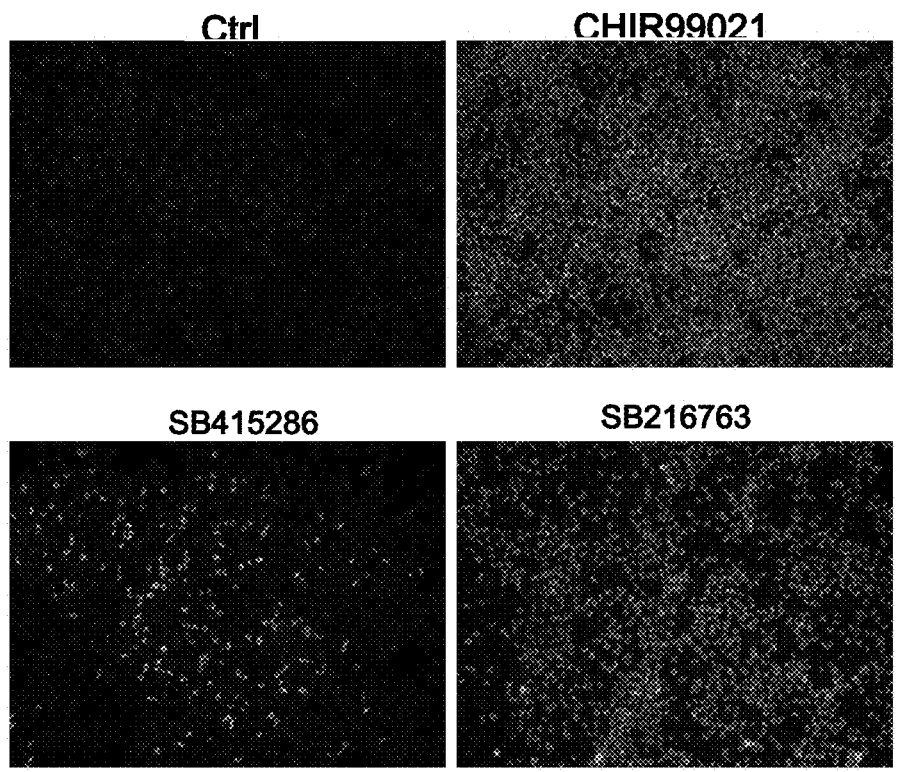
FIG. 13 shows the results of immunofluorescent staining, using an anti-human SOX17 antibody, of the cells obtained by cultivating with simultaneous addition of various GSK3 inhibitors with activin A in the present differentiation induction method, step (1) (differentiation induction from day 0 to day 1) for 1 day, and further cultivating according to step (2) for 2 days. The nuclei of SOX17-positive cells are colored green with Alexa 488, and the nuclei of the negative cells are colored blue with Hoechst 33342. When CHIR99021 (Example 32), SB415286 (Example 33) or SB216763 (Example 34) was added in combination with activin A, the ratio of SOX17-positive cells increased as compared to those of addition of activin A alone (control).

In Example 32, CHIR99021 was used; in Example 33, SB415286 was used; and in Example 34, SB216763 was used. To examine expression of SOX17 protein on day 3 of differentiation induction, immunofluorescent staining using an anti-SOX17 antibody was performed. 4% PFA was added to the cells on day 3 of culture under each condition, the mixture was incubated at room temperature for 30 min to fix the cells. The cells were sequentially reacted with anti-human SOX17 antibody (AF1924, R&D Systems) as the first antibody, and Alexa 488-labeled second antibody (Invitrogen) as the second antibody, and observed with a fluorescence microscope. The results are shown in FIG. 13. As shown in Example 1, when activin A and CHIR99021 were added (Example 32), most of the cells were observed to have expressed SOX17 protein. Furthermore, when activin A and SB415286 (Example 33) or activin A and SB216763 (Example 34) were added, the ratio of the cells expressing SOX17 protein was observed to have increased as compared to that with the addition of activin A alone (Comparative Example). From the above-mentioned investigation, it has been clarified that differentiation into endoderm can be induced even when a GSK3 inhibitor other than CHIR99021 is added simultaneously with activin A in step (1).

Examples 35-38

Induction of Differentiation of Endodermal Cells into Progenitor Cells of Pancreatic Hormone-Producing Cells by Using Retinoic Acid Receptor Agonist Other than Retinoic Acid [Step (3)]

Figure 14:
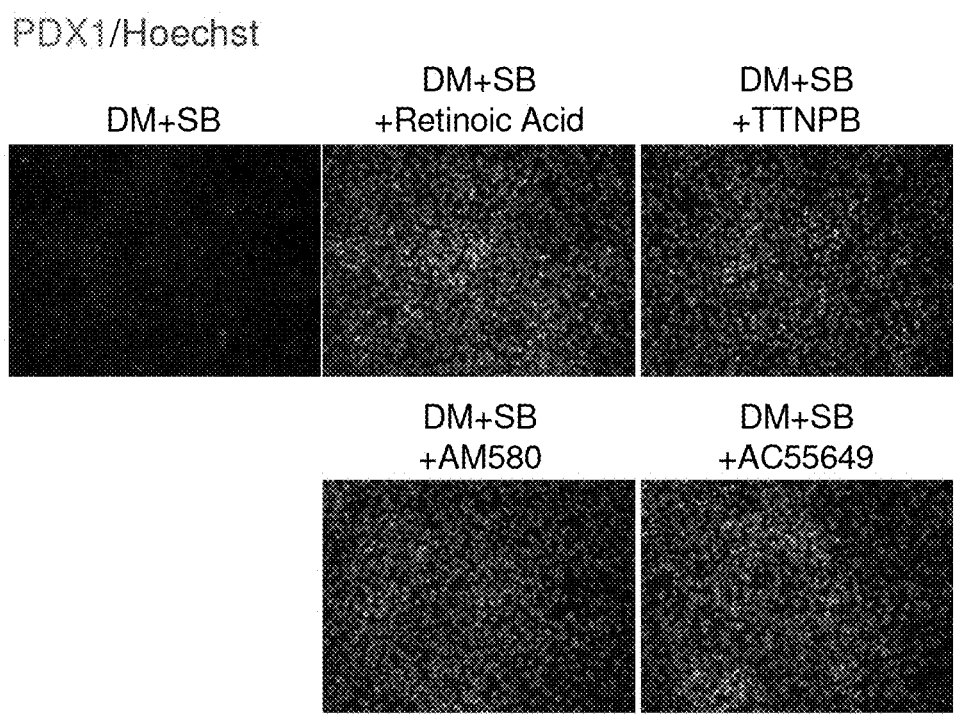
FIG. 14 shows the results of immunofluorescent staining, using an anti-PDX1 antibody, of the cells obtained by differentiation with simultaneous addition of various retinoic acid receptor agonists with dorsomorphin and SB431542, or addition of dorsomorphin and SB431542 alone as a control, in the present differentiation induction method, step (3) (differentiation induction from day 3 to day 10). In the Figure, DM shows dorsomorphin and SB shows SB431542. PDX1-positive cells are colored green with Alexa 488, and the nuclei of the cells are colored blue with Hoechst 33342. Simultaneously addition of various retinoic acid receptor agonists with dorsomorphin and SB431542 induced most of the cells into PDX1-positive cells.

Whether differentiation into progenitor cells of pancreatic hormone-producing cells can be induced even when a retinoic acid receptor agonist other than retinoic acid is used in step (3) was examined. The cell induced to differentiate into endodermal cells according to the method shown in Example 1 was washed with Improved MEM Zinc Option medium (Invitrogen), and the medium was changed to Improved MEM Zinc Option medium (Invitrogen) containing dorsomorphin (1 μM), SB431542 (10 μM) and 1% B-27 (GIBCO) and added with various retinoic acid receptor agonists. As the retinoic acid receptor agonist, retinoic acid (2 μM, Example 35), TTNPB (0.2 μM, Example 36), AM580 (0.2 μM, Example 37) and AC55649 (0.5 μM, Example 38) were used. In the control cells, the medium was changed to one without addition of a retinoic acid receptor agonist (control). After the medium exchange, the cells were cultured under the condition of 37° C., 5% $CO_2$ for 7 days. After the culture, the cells were fixed with 2% PFA for 10 min and further with 4% PFA for 20 min at room temperature. Then, the cells were sequentially reacted with an anti-human PDX1 antibody (AF2419, R&D Systems) as the first antibody, and further with an Alexa 488-labeled second antibody (Invitrogen) as the second antibody, and observed with a fluorescence microscope. The results of immunofluorescent staining are shown in FIG. 14. Most of the cells were differentiated into PDX1-positive cells by simultaneous addition of dorsomorphin and SB431542 irrespective of the retinoic acid receptor agonist added. From these results, it has been clarified that differentiation into progenitor cells of pancreatic hormone-producing cells can be induced even when a retinoic acid receptor agonist other than retinoic acid is used in step (3).

Examples 39-43

Induction of Differentiation of Endodermal Cell into Progenitor Cells of Pancreatic Hormone-Producing Cells by Using Noggin Instead of Dorsomorphin [Step (3)]

Figure 15:
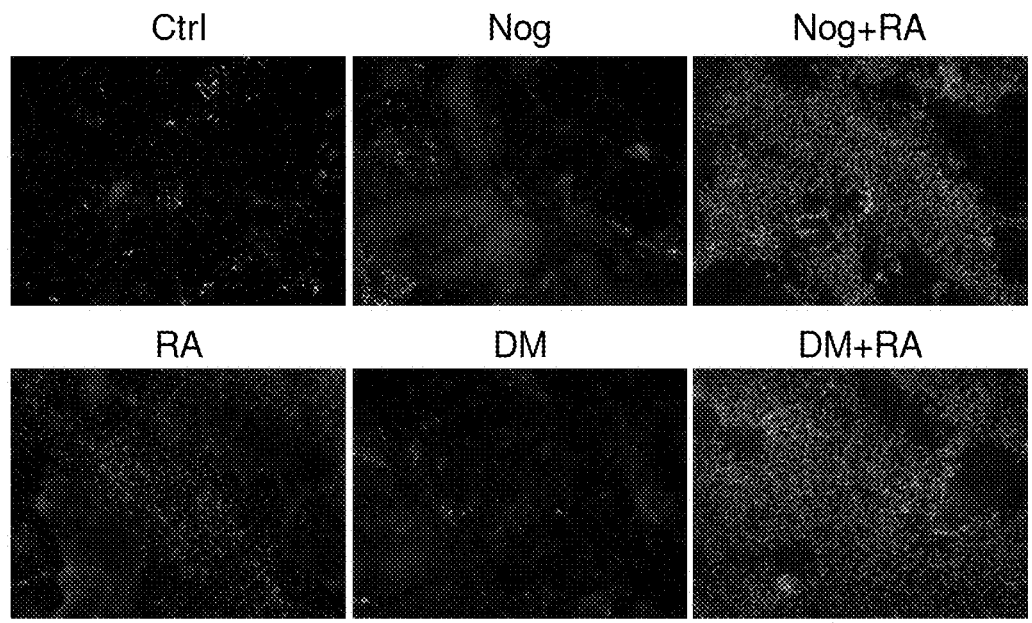
FIG. 15 shows differentiation induced by the addition of Noggin, retinoic acid or dorsomorphin each alone, or a combination of Noggin and retinoic acid or a combination of dorsomorphin and retinoic acid, in the present differentiation induction method, step (3) (differentiation induction from day 3 to day 10). In addition, a part of the cells was cultured without addition of an inducing factor as a control. The results of immunofluorescent staining, using an anti-PDX1 antibody, of the cells after culture are shown. In the Figure, Ctrl shows a control without addition of an inducing factor, Nog shows Noggin, RA shows retinoic acid, and DM shows dorsomorphin. PDX1-positive cells are colored green with Alexa 488, and the nuclei of the cells are colored blue with Hoechst 33342. When a combination of Noggin and retinoic acid or a combination of dorsomorphin and retinoic acid was added, many cells were induced into PDX1-positive cells.

One of the known activities of dorsomorphin is shutting off of BMP signal by inhibiting ALK-2,3,6. Whether differentiation into progenitor cells of pancreatic hormone-producing cells can be induced even when Noggin, similarly known to shut off BMP signal, is used in step (3) instead of dorsomorphin was examined. The cells induced to differentiate into an endodermal cells according to the method shown in Example 1 was washed with Improved MEM Zinc Option medium (Invitrogen), and the medium was changed to Improved MEM Zinc Option medium (Invitrogen) containing 1% B-27 (GIBCO) and added with retinoic acid (2 μM) (Example 39), a medium added with Noggin (100 ng/ml) (Example 40), a medium added with dorsomorphin (1 μM) (Example 41), a medium added with Noggin and retinoic acid (Example 42), and a medium added with dorsomorphin and retinoic acid (Example 43). For the control cells, the medium was changed to one without addition of the aforementioned inducing factors (Ctrl). After the medium exchange, the cells were cultured under the condition of 37° C., 5% $CO_2$ for 7 days. After the culture, the cells were fixed with 2% PFA for 10 min and further with 4% PFA for 20 min at room temperature. Then, the cells were sequentially reacted with an anti-human PDX1 antibody (AF2419, R&D Systems) as the first antibody, and further with an Alexa 488-labeled second antibody (Invitrogen) as the second antibody, and observed with a fluorescence microscope. The results of immunofluorescent staining are shown in FIG. 15. When Noggin and retinoic acid were simultaneously added, differentiation into a PDX1-positive cells was remarkably induced, as with the simultaneous addition of dorsomorphin and retinoic acid. It has been clarified that shutting off of BMP signal simultaneously with the addition of retinoic acid is important for differentiation induction into pancreatic progenitor cells.

Examples 44-47

Induction of Differentiation of Endodermal Cells into Progenitor Cells of Pancreatic Hormone-Producing Cells by Using Inhibitor of Activin Receptor-Like Kinase-4,5,7 Other than SB431542 [Step (3)]

Figure 16:
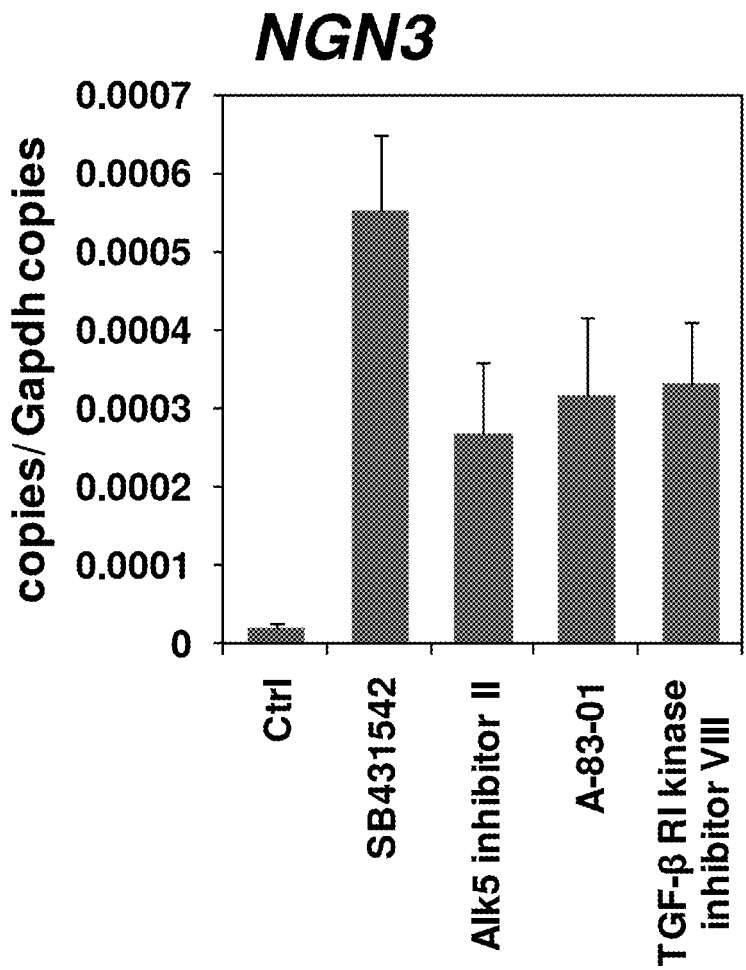
FIG. 16 shows the results of the measurement of the expression level of NGN3 by quantitative RT-PCR in the cells obtained by cultivation with simultaneous addition of various inhibitors of activin receptor-like kinase-4,5,7 with dorsomorphin and retinoic acid, or addition of dorsomorphin and retinoic acid alone as a control, in the present differentiation induction method, step (3) (differentiation induction from day 3 to day 10). The results are shown as relative values to the expression level of a housekeeping gene GAPDH. Any inhibitor of activin receptor-like kinase-4,5,7 increased the expression of NGN3 by simultaneous addition of dorsomorphin and retinoic acid.

Whether differentiation into progenitor cells of pancreatic hormone-producing cells can be induced even when an inhibitor of activin receptor-like kinase-4,5,7 other than SB431542 is used in step 3 was examined. The cells induced to differentiate into an endodermal cells according to the method shown in Example 1 was washed with Improved MEM Zinc Option medium (Invitrogen), and the medium was changed to Improved MEM Zinc Option medium (Invitrogen) containing dorsomorphin (1 μM), retinoic acid (2 μM) and 1% B-27 (GIBCO) and added with various inhibitors of activin receptor-like kinase-4,5,7. As the inhibitor of activin receptor-like kinase-4,5,7, ALK5 inhibitor II (2 μM, Example 45), A-83-01 (0.2 μM, Example 46) and TGFβRI kinase inhibitor VIII (0.2 μM, Example 47) were used besides SB431542 (5 μM, Example 44). As a control, the medium was changed to one added with dorsomorphin and retinoic acid alone (Ctrl). After the medium exchange, the cells were cultured under the condition of 37° C., 5% $CO_2$ for 7 days. After the culture, the expression level of NGN3, which is progenitor cells of pancreatic hormone-producing cells marker, was measured in the same manner as in Example 1. The results of the experiment are shown in FIG. 16. By simultaneous addition of dorsomorphin and retinoic acid, the expression of NGN3 increased remarkably irrespective of the inhibitor of activin receptor-like kinase-4,5,7 added. From these results, it has been clarified that differentiation into progenitor cells of pancreatic hormone-producing cells can be induced even when an inhibitor of activin receptor-like kinase-4,5,7 other than SB431542 is used in step (3).

Examples 48-54

Induction of Differentiation of Progenitor Cells of Pancreatic Hormone-Producing Cells into Pancreas Cells [Step (4); Treatment with Camp Phosphodiesterase Inhibitor, cAMP Analog, Inhibitor of Activin Receptor-Like Kinase-4,5,7]

Forskolin used for induction of differentiation of insulin-producing cells is known to have an intracellular cAMP-increasing action. Whether differentiation into insulin-producing cells can be induced even when IBMX, which is a cAMP phosphodiesterase inhibitor or dibutyl cAMP, which is a cAMP analog, similarly known to increase intracellular cAMP by their addition was examined. In addition, ALK5 inhibitor II used for induction of differentiation into insulin-producing cells is also known as an inhibitor of activin receptor-like kinase-4,5,7. Whether differentiation into insulin-producing cells can be induced even when other inhibitor of activin receptor-like kinase-4,5,7 is added was examined in the same manner.

Figure 17:
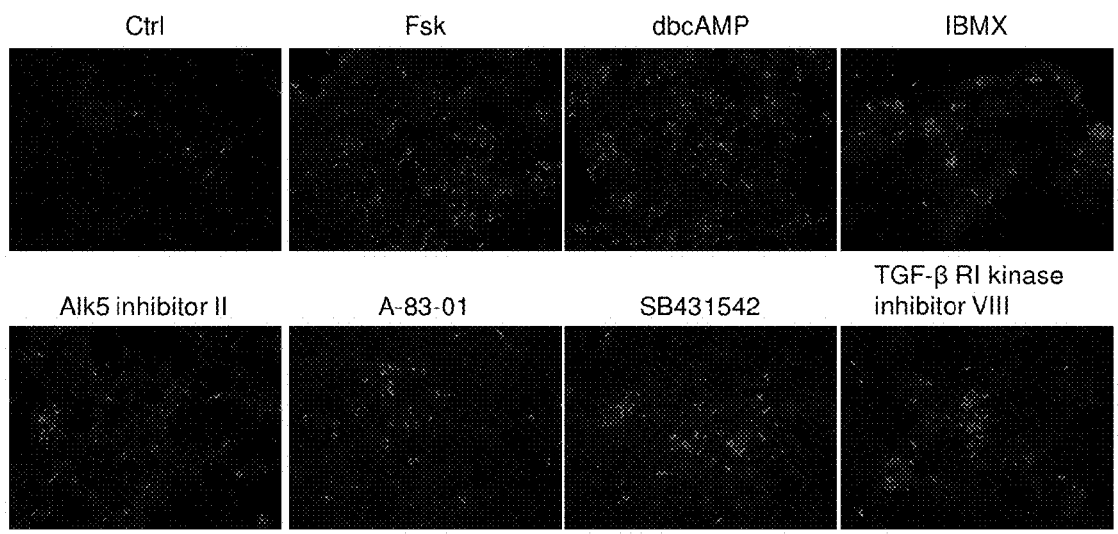
FIG. 17 shows the results of immunofluorescent staining, using an anti-insulin antibody, of the cells obtained by cultivation with the addition of each of forskolin (Fsk), dibutyl cAMP (dbcAMP), IBMX, ALK5 inhibitor II, A-83-01, SB431542 and TGFβRI kinase inhibitor VIII, or without addition of an inducing factor as a control (Ctrl), in the present differentiation induction method, step (4) (differentiation induction from day 10 to day 21). The insulin-positive cells are colored red with Alexa 568, and the nuclei of the cells are colored blue with Hoechst 33342. The cultivation with the addition of these compounds induced differentiation into insulin-positive cells with high efficiency.

Endodermal cells were induced according to the method shown in Example 1, 3 kinds of dorsomorphin (1 μM), retinoic acid (2 μM) and SB431542 (10 μM) were simultaneously added to Improved MEM Zinc Option medium (Invitrogen) containing 1% B-27, and the cells were cultured for 7 days. The medium was changed once on day 7 of induction. The cells on day 10 of induction were washed with Improved MEM Zinc Option medium, the medium was changed to Improved MEM Zinc Option medium containing 1% B-27 (GIBCO) and added with forskolin (10 μM) (Example 48), a medium added with dibutyl cAMP (500 μM) (Example 49), a medium added with IBMX (200 μM) (Example 50), a medium added with ALK5 inhibitor II (5 μM) (Example 51), a medium added with A-83-01 (0.5 μM) (Example 52), a medium added with SB431542 (10 μM) (Example 53), and a medium added with TGFβRI kinase inhibitor VIII (2 μM) (Example 54), or a medium without addition of the aforementioned inducing factors as a control, and the cells were further cultured for 11 days. The medium was changed every 3-4 days. After culture, the cells were fixed with 2% PFA for 10 min and further with 4% PFA for 20 min at room temperature. Thereafter, the cells were sequentially reacted with an anti-insulin antibody (A0564, DAKO) as the first antibody, and with Alexa 568-labeled second antibody (Invitrogen) as the second antibody, and observed with a fluorescence microscope. The results of the experiment are shown in FIG. 17. It was observed that the positive rate of insulin-expressing cells remarkably increased when dibutyl cAMP, IBMX, A-83-01, SB431542 or TGFβRI kinase inhibitor VIII was added, like the addition of forskolin or ALK5 inhibitor II. From these results, it has been clarified that differentiation of progenitor cells of pancreatic hormone-producing cells into insulin-producing cells can be induced by enhancing intracellular cAMP signal or inhibiting activin receptor-like kinase-4,5,7.

Examples 55-58

Induction of Differentiation of Progenitor Cells of Pancreatic Hormone-Producing Cells into Pancreas Cells [Step (4); Treatment with Steroid]

Dexamethasone used for induction of differentiation into insulin-producing cells is known to be one kind of steroid. Whether differentiation into insulin-producing cells can be induced even when other steroid is added was examined.

Figure 18:
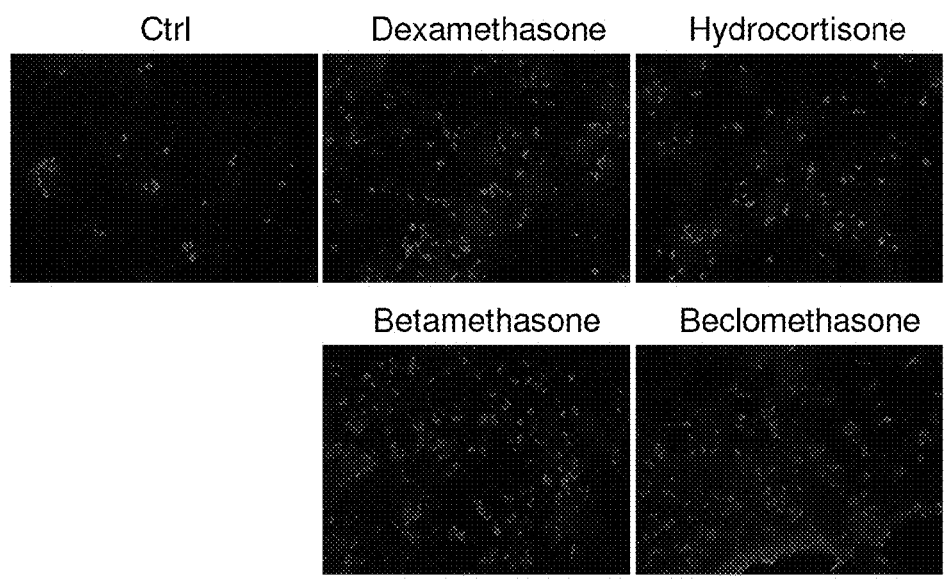
FIG. 18 shows the results of immunofluorescent staining, using an anti-insulin antibody, of the cells obtained by cultivation with the addition of each of dexamethasone, hydrocortisone, betamethasone and beclomethasone, or without addition of an inducing factor as a control (Ctrl), in the present differentiation induction method, step (4) (differentiation induction from day 10 to day 21). The insulin-positive cells are colored red with Alexa 568, and the nuclei of the cells are colored blue with Hoechst 33342. The cultivation with the addition of these compounds induced differentiation into insulin-positive cells with high efficiency.

Endodermal cells were induced according to the method shown in Example 1, 3 kinds of dorsomorphin (1 μM), retinoic acid (2 μM) and SB431542 (10 μM) were simultaneously added to Improved MEM Zinc Option medium (Invitrogen) containing 1% B-27, and the cells were cultured for 7 days. The medium was changed once on day 7 of induction. The cells on day 10 of induction were washed with Improved MEM Zinc Option medium, the medium was changed to Improved MEM Zinc Option medium containing 1% B-27 (GIBCO) and added with dexamethasone (10 μM) (Example 55), a medium added with hydrocortisone (5 μM) (Example 56), a medium added with betamethasone (2 μM) (Example 57), and a medium added with beclomethasone (1 μM) (Example 58), or a medium without addition of the aforementioned inducing factors as a control, and the cells were further cultured for 11 days. The medium was changed every 3-4 days. After culture, the cells were fixed with 2% PFA for 10 min and further with 4% PFA for 20 min at room temperature. Thereafter, the cells were sequentially reacted with an anti-insulin antibody (A0564, DAKO) as the first antibody, and with Alexa 568-labeled second antibody (Invitrogen) as the second antibody, and observed with a fluorescence microscope. The results of the experiment are shown in FIG. 18. It was observed that the positive rate of insulin-expressing cells remarkably increased when hydrocortisone, betamethasone or beclomethasone was added, like the addition of dexamethasone. From these results, it has been clarified that differentiation of progenitor cells of pancreatic hormone-producing cells into insulin-producing cells can be induced by adding steroid.

Example 59

Insulin Secretion in Differentiated Insulin-Producing Cells in Response to Various Stimulations It is known that pancreatic β cells in the body extracellularly secrete insulin in response to various stimulations. Whether insulin-producing cells differentiated by the present differentiation induction method secrete insulin in response to various stimulations was examined.

Figure 19:
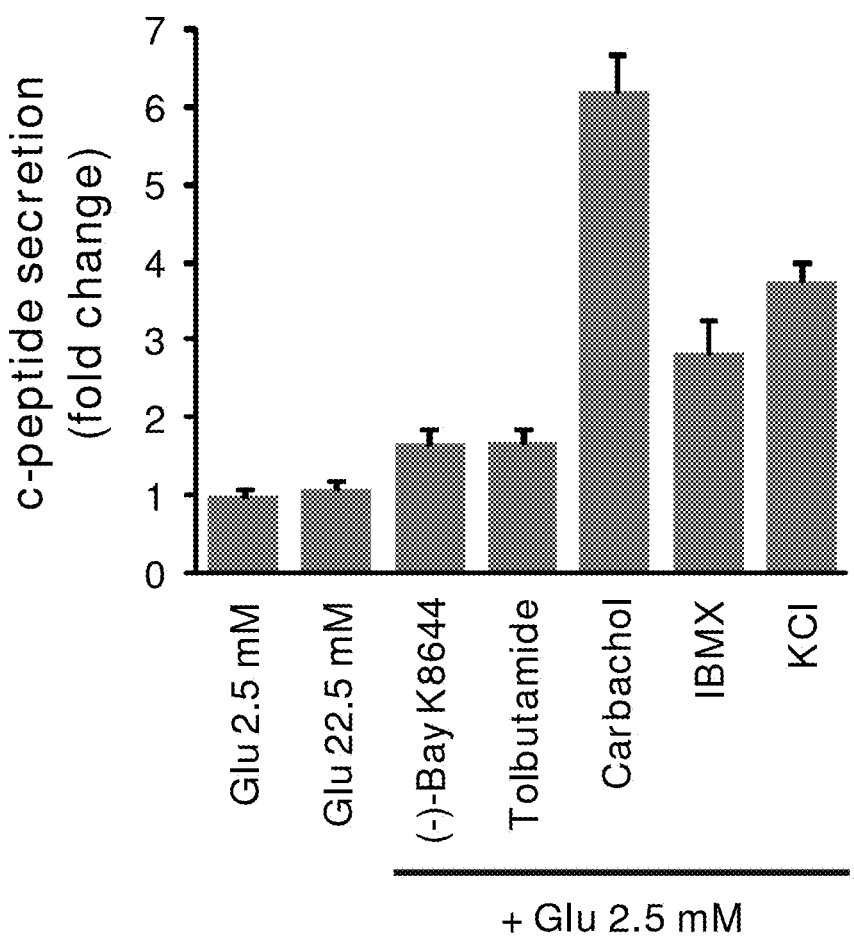
FIG. 19 shows measurement of the amount of C-peptide secreted in the supernatant when the cells subjected to differentiation induction according to the present differentiation induction method was added over 1 hr with various factors that promote insulin secretion. The values in the Figure are relative values to the secretion amount of C-peptide with the addition of 2.5 mM glucose as the standard. The addition of various compounds to a buffer containing 2.5 mM glucose increased extracellular secretion of C-peptide.

Endodermal cells were induced according to the method shown in Example 1, 3 kinds of dorsomorphin (1 μM), retinoic acid (2 μM) and SB431542 (10 μM) were simultaneously added to Improved MEM Zinc Option medium (Invitrogen) containing 1% B-27, and the cells were cultured for 7 days. The medium was changed once on day 7 of induction. The cells on day 10 of induction were washed with Improved MEM Zinc Option medium, the medium was changed to Improved MEM Zinc Option medium containing 1% B-27 (GIBCO) and added with forskolin (10 μM), nicotinamide (10 mM), dexamethasone (10 μM) and ALK5 inhibitor II (5 μM), and the cells were further cultured for 11 days. The medium was changed every 3-4 days. After the culture, the cells were washed with a buffer containing 2.5 mM glucose (NaCl (116 mM), KCl (4.7 mM), KH$_2$PO$_4$ (1.18 mM), MgSO$_4$ (1.18 mM), NaHCO$_3$ (25 mM), CaCl$_2$ (2.52 mM), HEPES (24 mM), 0.1% BSA), a buffer containing 2.5 mM glucose was added and the mixture was cultured at 37° C. for 2 hr. The supernatant was completely removed, and a buffer containing 2.5 mM glucose, a buffer containing 22.5 mM glucose, a buffer containing 2.5 mM glucose and 2 μM (−)-Bay K8644, a buffer containing 2.5 mM glucose and 100 μM tolbutamide, a buffer containing 2.5 mM glucose and 250 μM carbachol, a buffer containing 2.5 mM glucose and 0.5 mM IBMX, and a buffer containing 2.5 mM glucose and 30 mM KCl were respectively added. After culture at 37° C. for 1 hr, the culture supernatant was recovered, and the C-peptide contained in the culture supernatant was measured using Human C-peptide ELISA kit (Mercodia AB). The results are shown in FIG. 19. The C-peptide secretion level increased when (−)-Bay K8644, tolbutamide, carbachol, IBMX and KCl were added. From these results, it has been clarified that the insulin-producing cells differentiated by the method of the present invention secretes insulin extracellularly in response to various stimulations.

Example 60

Figure 20:
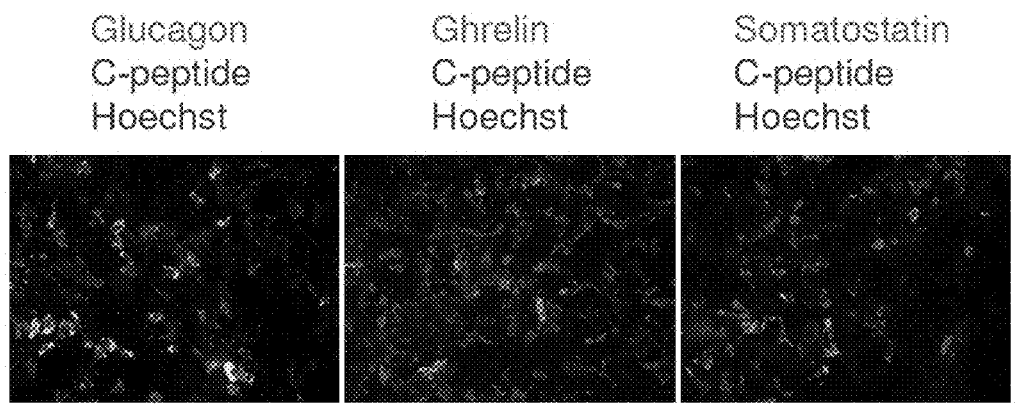
FIG. 20 shows the results of immunofluorescent staining, using an anti-glucagon antibody, an anti-ghrelin antibody, an anti-somatostatin antibody, and an anti-C-peptide antibody, of the cells on day 21 of culture for differentiation induction according to the present differentiation induction method. The glucagon-positive cells, the ghrelin-positive cells, and the somatostatin-positive cells are colored green with Alexa 488, C-peptide-positive cells are colored red with Alexa 568, and the nuclei of the cells are colored blue with Hoechst 33342. Using the present differentiation induction method, not only C-peptide-positive cells, but also glucagon-positive cells, ghrelin-positive cells and somatostatin-positive cells were simultaneously induced.

Differentiation into Pancreatic Hormone-Producing Cells Other than Insulin-Producing Cells Whether pancreatic hormone-producing cells other than insulin-producing cells are simultaneously differentiated by the present differentiation induction method was examined. Endodermal cells were induced according to the method shown in Example 1, 3 kinds of dorsomorphin (1 μM), retinoic acid (2 μM) and SB431542 (10 μM) were simultaneously added to Improved MEM Zinc Option medium (Invitrogen) containing 1% B-27, and the cells were cultured for 7 days. The medium was changed once on day 7 of induction. The cells on day 10 of induction were washed with Improved MEM Zinc Option medium, the medium was changed to Improved MEM Zinc Option medium containing 1% B-27 (GIBCO) and added with forskolin (10 μM), nicotinamide (10 mM), dexamethasone (10 μM) and ALK5 inhibitor II (5 μM), and the cells were further cultured for 11 days. The medium was changed every 3-4 days. After the culture, the cells were fixed with 2% PFA for 10 min, and further with 4% PFA for 20% min at room temperature. Then, the cells were sequentially reacted with an anti-human C-peptide antibody (C-PEP-01, MONOSAN), an anti-glucagon antibody (SC-7780, Santa Cruz Biotechnology, Inc.), an anti-ghrelin antibody (SC-10368, Santa Cruz Biotechnology, Inc.) or an anti-somatostatin antibody (A0566, DAKO) as the first antibody, and further with Alexa 488-labeled second antibody (Invitrogen) or Alexa 568-labeled second antibody (Invitrogen) as the second antibody, and the cells were observed with a fluorescence microscope. The results of immunofluorescent staining are shown in FIG. 20. In addition to C-peptide-positive cells, glucagon-positive cells, ghrelin-positive cells and somatostatin-positive cells were observed. It has been confirmed that pancreatic hormone-producing cells other than insulin-producing cells are simultaneously induced by the present differentiation induction method.

Example 61

Induction of Differentiation from Plural Human iPS Cell Lines into Insulin-Producing Cell In the aforementioned Examples, 253G1 strain was used as a human iPS cell line. Whether differentiation into a pancreas cell can be induced from a human iPS cell line other than 253G1 strain was examined. As the human iPS cell line, 253G1 strain (iPS cell line produced by expression of OCT4/SOX2/KLF4 in skin fibroblast of 36-year-old female), as well as 201B7 strain (iPS cell line produced by expression of OCT4/SOX2/KLF4/c-MYC in skin fibroblast of 36-year-old female), 1503-iPS(297A1) (iPS cell line produced by expression of OCT4/SOX2/KLF4/c-MYC in skin fibroblast of 73-year-old female), 1392-iPS(297F1) (iPS cell line produced by expression of OCT4/SOX2/KLF4/c-MYC in skin fibroblast of 56-year-old male), or NHDF-iPS(297L1) (iPS cell line produced by expression of OCT4/SOX2/KLF4/c-MYC in skin fibroblast of newborn boy) were used to induce differentiation (see Cell 2007; 131(5), p861-72, PLoS ONE 2009; 4(12), p.e8067).

Figure 21:
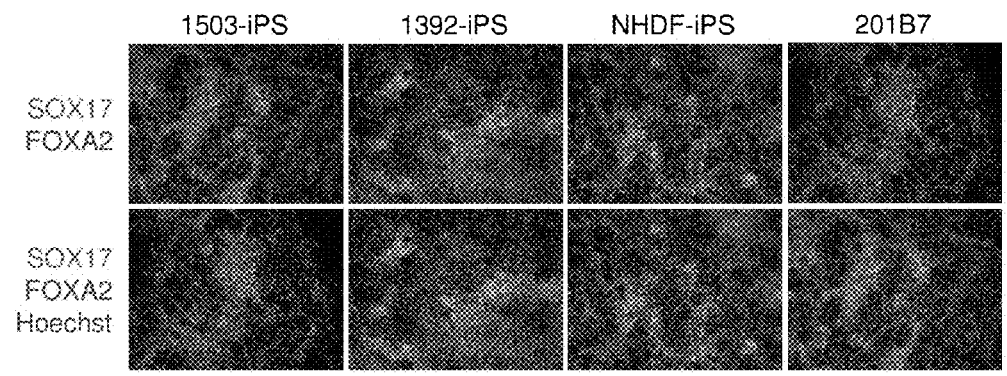
FIG. 21 shows induction of an endoderm from a different human iPS cell line according to the present differentiation induction method. The results of immunofluorescent staining, using an anti-SOX17 antibody and an anti-FOXA2 antibody, of the cells on day 3 of culture are shown. SOX17-positive cells are colored green with Alexa 488, FOXA2-positive cells are colored red with Alexa 568, and the nuclei of the cells are colored blue with Hoechst 33342. Using the present differentiation induction method, an SOX17-positive and FOXA2-positive endoderm was efficiently induced from all human iPS cell lines.

According to the method shown in Example 1, differentiation into endoderm was induced. To examine expression of SOX17 and FOXA2 protein after culture for 3 days, immunofluorescent staining using an anti-SOX17 antibody and an anti-FOXA2 antibody was performed. After culture up to day 3 in the same manner as in Example 1, the cells were fixed with 2% PFA for 10 min and further for 20 min with 4% PFA at room temperature. The cells were reacted with an anti-human SOX17 antibody (AF1924, R&D Systems) and anti-FOXA2 antibody (07-633, Millipore) as the first antibody, sequentially reacted with an Alexa 488-labeled second antibody (Invitrogen) or an Alexa 568-labeled second antibody (Invitrogen) as the second antibody, and observed with a fluorescence microscope. The results are shown in FIG. 21. It was observed that most of the cells were differentiated into SOX17-positive and FOXA2-positive endoderm cells even when 201B7 strain, 1503-iPS (297A1) strain, 1392-iPS (297F1) strain or NHDF-iPS (297L1) strain was used for differentiation.

Figure 22:
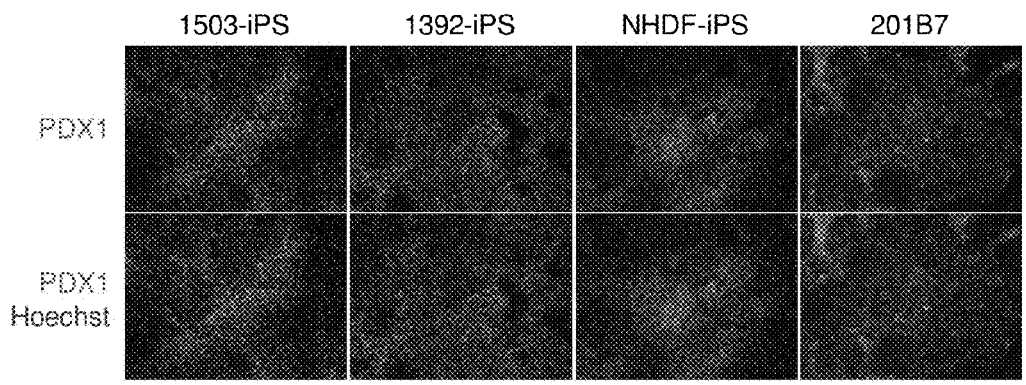
FIG. 22 shows induction of pancreatic progenitor cells from a different human iPS cell line according to the present differentiation induction method. The results of immunofluorescent staining, using an anti-PDX1 antibody, of the cells on day 10 of culture after differentiation induction are shown. PDX1-positive cells are colored green with Alexa 488, and the nuclei of the cells are colored blue with Hoechst 33342. Using the present differentiation induction method, a PDX1-positive pancreatic progenitor cells were efficiently induced from all human iPS cell lines.

After induction into endodermal cells, the cells were cultured for 7 days in Improved MEM Zinc Option medium (Invitrogen) containing 1% B-27, and simultaneously added with 3 kinds of dorsomorphin (1 μM), retinoic acid (2 μM) and SB431542 (10 μM). The medium was changed every 7 days. After the culture, the cells were fixed with 2% PFA for 10 min and further with 4% PFA for 20 min at room temperature. Then, the cells were sequentially reacted with an anti-human PDX1 antibody (AF2419, R&D Systems) as the first antibody, and further with an Alexa 488-labeled second antibody (Invitrogen) as the second antibody, and observed with a fluorescence microscope. The results of immunofluorescent staining are shown in FIG. 22. It was observed that most of the cells were differentiated into PDX1-positive progenitor cells of pancreatic hormone-producing cells even when 201B7 strain, 1503-iPS(297A1) strain, 1392-iPS(297F1) strain or NHDF-iPS(297L1) strain was used for differentiation.

Figure 23:
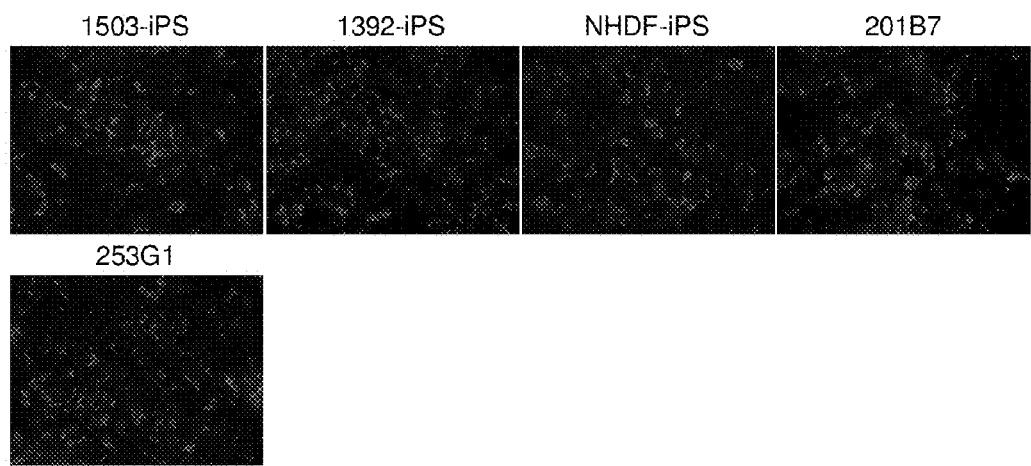
FIG. 23 shows induction of insulin-producing cells from a different human iPS cell line according to the present differentiation induction method. The results of immunofluorescent staining, using an anti-insulin antibody, of the cells on day 21 of culture after differentiation induction are shown. The insulin-positive cells are colored red with Alexa 568, and the nuclei of the cells are colored blue with Hoechst 33342. Using the present differentiation induction method, differentiation into insulin-producing cells was efficiently induced from all human iPS cell lines.

The cells on day 10 of induction were washed with Improved MEM Zinc Option medium, the medium was changed to Improved MEM Zinc Option medium containing 1% B-27 (GIBCO) and added with forskolin (10 μM), nicotinamide (10 mM), dexamethasone (10 μM), ALK5 inhibitor II (5 μM), and the cells were further cultured for 11 days. The medium was changed every 3-4 days. After the culture, the cells were fixed with 2% PFA for 10 min and further with 4% PFA for 20 min at room temperature. Then, the cells were sequentially reacted with an anti-insulin antibody (A0564, DAKO) as the first antibody, and further with an Alexa 568-labeled second antibody (Invitrogen) as the second antibody, and observed with a fluorescence microscope. The results of immunofluorescent staining are shown in FIG. 23. Like 253G1 strain, it was observed that differentiation into insulin-producing cells was efficiently induced even when differentiated from 201B7 strain, 1503-iPS(297A1) strain, 1392-iPS (297F1) strain or NHDF-iPS(297L1). From the above results, it has been clarified that differentiation into insulin-producing cells can be induced by using the present differentiation induction method, irrespective of the kind of the human iPS cell line.

Examples 62-64

Method of Inducing Human iPS Cells into Pancreatic Hormone-Producing Cells by Substituting Feeder Cells with Fibronectin or Matrigel Whether differentiation into pancreatic hormone-producing cells can be induced even when fibronectin or Matrigel is used as a substitute for feeder cells in the present differentiation induction system was examined. When fibronectin is used as a substitute, 50 μl of human plasma fibronectin (Invitrogen) diluted 40-fold with DMEM/F12 medium was added to a 96 well plate, left standing at room temperature for 3 hr or more and removed for use. On the other hand, when Matrigel is used as a substitute, 50 μl of Matrigel-growth factor reduced mouse (COLLABORATIVE RESEARCH, INC.) diluted 60-fold with DMEM/F12 medium was added to a 96 well plate, left standing at room temperature for 3 hr or more and removed for use. iPS cells maintained in a cell mass was treated with 0.25% trypsin-1 mM EDTA solution (GIBCO) and dissociated until they became single cells. Then, iPS cells dispersed in a medium were seeded in a 96 well plate coated with fibronectin or Matrigel, at a density of $4 \times 10^4$ cells per well and cultured at 37° C. in 5% $CO_2$ for 1 day. As a culture medium for seeding, a medium for primate ES cells added with 10 μM Y-27632 (Wako Pure Chemical Industries, Ltd.) was used. One day after seeding, the medium was changed to a medium for primate ES cells without Y-27632, and the cells were further cultured for 2 days until they became confluent. After the culture, the cells were washed with RPMI medium (GIBCO), and cultured in RPMI medium added with CHIR99021, 2% FBS and activin A (100 ng/ml) for 1 day. After culture for 1 day, the cells were washed with RPMI medium, and further cultured in RPMI medium added with 2% FBS and 100 ng/ml activin A for 2 days. Then, the cells were cultured for 7 days in Improved MEM Zinc Option medium (Invitrogen) containing 1% B-27 and simultaneously added with 3 kinds of dorsomorphin (1 μM), retinoic acid (2 μM) and SB431542 (10 μM). The medium was changed once on day 7 of induction. The cells on day 10 of induction were washed with Improved MEM Zinc Option medium, the medium was changed to Improved MEM Zinc Option medium containing 1% B-27 (GIBCO) and added with forskolin (10 μM), nicotinamide (10 mM), dexamethasone (10 μM) and ALK5 inhibitor II (5 μM), and the cells were further cultured for 11 days. The medium was changed every 3-4 days, whereby pancreatic hormone-producing cells were induced.

When pancreatic hormone-producing cells were induced on feeder cells are Example 62, when pancreatic hormone-producing cells were induced on fibronectin is Example 63, and when pancreatic hormone-producing cells were induced on Matrigel is Example 64. RNA was recovered from the cells on day 0 and day 21 of induction, and the expression level of insulin mRNA was measured in the same manner as in the method shown in Example 1. The results are shown in Table 1. The insulin mRNA expression increased under any conditions as the number of the days of culture increased. From these results, it has been clarified that pancreatic hormone-producing cells can be induced by the present differentiation induction method, even in a culture system using fibronectin or Matrigel as a coating agent instead of feeder cells.

TABLE 1

|  | insulin mRNA expression level on day 0 of induction (Copies/GAPDH copies) | insulin mRNA expression level on day 21 of induction (Copies/GAPDH copies) |
|---|---|---|
| Feeder (Ex. 62) | 0.00002 | 0.240 |
| Fibronectin (Ex. 63) | 0.00006 | 0.072 |
| Matrigel (Ex. 64) | 0.00011 | 0.189 |

This application is based on patent application Nos. 2009-299276, and 2010-144283 filed in Japan, the contents of which are incorporated in full herein.

Industrial Applicability

According to the production method of the present invention, pancreas cells, particularly pancreatic hormone-producing cells, can be produced more efficiently from stem cells. The pancreatic hormone-producing cells obtained by the production method can be used for screening for a compound useful for the prophylaxis and/or treatment of a disease (e.g., diabetes) caused by abnormal production and/or secretion of pancreatic hormones. Furthermore, a medicament containing pancreatic hormone-producing cells obtained by the production method of the present invention can be used for treating such disease.

The invention claimed is:

1. A method of producing pancreatic hormone-producing cells, comprising:
   (i) culturing human or mouse induced-pluripotent stem (iPS) cells, in a medium containing an activator of activin receptor-like kinase-4,7 and a GSK3 inhibitor,
   (ii) culturing the cells of step (i) in a medium containing an activator of activin receptor-like kinase-4,7,
   (iii) culturing the cells obtained in step (ii) in a medium containing the following (a)-(c):
      (a) retinoic acid receptor agonists,
      (b) at least one kind selected from the group consisting of inhibitors of AMP-activated protein kinase and/or activin receptor-like kinase-2,3,6, and BMP antagonists, and
      (c) inhibitors of activin receptor-like kinase-4,5,7, and
   (iv) culturing the cells obtained from step (iii) in a medium containing any factor selected from the group consisting of (ia) at least one kind selected from the group consisting of adenylate cyclase activators, cAMP phosphodiesterase inhibitors and cAMP analogs, (ib) steroids and (ic) inhibitors of activin receptor-like kinase-4,5,7 to obtain pancreatic hormone-producing cells.

2. The method according to claim 1, wherein the activator of activin receptor-like kinase-4,7 in steps (i) and (ii) is activin, and step (iii) is a step of culturing the cell(s) obtained in step (ii) in a medium containing any one or more kinds selected from the group consisting of (a) retinoic acid receptor agonists, (b) inhibitors of AMP-activated protein kinase and/or activin receptor-like kinase-2,3,6 and (c) inhibitors of activin receptor-like kinase-4,5,7.

3. The method according to claim 1, wherein the GSK3 inhibitor in step (i) is 6-[[2-[[4-(2,4-dichlorophenyl)-5-(4-methyl-1H-imidazol-2-yl)-2-pyrimidinyl]amino]ethyl]amino]nicotinonitrile.

4. The method according to claim 1, wherein the inhibitor of activin receptor-like kinase-4,5,7 in step (iii) is 4[4-(1,3-benzodioxol-5-yl)-5-(2-pyridinyl)-1H-imidazol-2-yl]-benzamide or a hydrate thereof.

5. The method according to claim 1, wherein said at least one kind selected from the group consisting of inhibitors of AMP-activated protein kinase and/or activin receptor-like kinase-2,3,6, and BMP antagonists in step (iii) is dorsomorphin or Noggin.

6. The method according to claim 1, wherein the medium in step (iii) contains retinoic acid, 4-[4-(1,3-benzodioxl-5-yl)-5 (2-pyridinyl)-1H-imidazol-2-yl]-benzamide or a hydrate thereof, and dorsomorphin.

7. The method according to claim 1, wherein at least one kind selected from the group consisting of adenylate cyclase activators, cAMP phosphodiesterase inhibitors and cAMP analogs is forskolin, 3-isobutyl-1-methylxanthine or dibutyl cAMP.

8. The method according to claim 1, wherein the steroid is dexamethasone.

9. The method according to claim 1, wherein the inhibitor of activin receptor-like kinase-4,5,7 is 2-(3-(6-methylpyridin-2-yl)-1H-pyrazol-4-yl)-1,5-naphthyridine, or 4-[4-(1,3-benzodioxol -5-yl)-5-(2-pyridinyl)-1H-imidazol-2-yl]-benzamide or a hydrate thereof.

10. The method of claim 1, wherein the medium in step (iv) contains nicotinamide.

\* \* \* \* \*